United States Patent
Koyama et al.

(10) Patent No.: US 7,938,814 B2
(45) Date of Patent: May 10, 2011

(54) DISPOSABLE DIAPER

(75) Inventors: Takao Koyama, Tochigi (JP); Hidekazu Ito, Tochigi (JP); Hiroshi Inada, Tochigi (JP); Takahiro Arimura, Tochigi (JP)

(73) Assignee: Kao Corporation, Tokyo (JP)

( * ) Notice: Subject to any disclaimer, the term of this patent is extended or adjusted under 35 U.S.C. 154(b) by 238 days.

(21) Appl. No.: 12/145,404

(22) Filed: Jun. 24, 2008

(65) Prior Publication Data

US 2008/0312626 A1 Dec. 18, 2008

Related U.S. Application Data

(62) Division of application No. 10/466,692, filed as application No. PCT/JP02/09367 on Sep. 12, 2002, now abandoned.

(30) Foreign Application Priority Data

| Sep. 21, 2001 | (JP) | ................................ | 2001-289941 |
| Nov. 12, 2001 | (JP) | ................................ | 2001-346577 |
| Nov. 15, 2001 | (JP) | ................................ | 2001-349620 |
| Dec. 4, 2001 | (JP) | ................................ | 2001-369516 |
| Dec. 13, 2001 | (JP) | ................................ | 2001-380516 |

(51) Int. Cl.
*A61F 13/15* (2006.01)

(52) U.S. Cl. ....... 604/385.24; 604/385.01; 604/385.101; 604/378; 604/380; 604/385.25; 604/385.26

(58) Field of Classification Search ............. 604/385.24, 604/385.01, 385.101, 378, 380, 385.25, 385.26
See application file for complete search history.

(56) References Cited

U.S. PATENT DOCUMENTS

| 3,744,494 A | 7/1973 | Marsan |
| 4,410,324 A | 10/1983 | Sabee |
| 5,087,506 A | 2/1992 | Palumbo et al. |
| 5,453,323 A | 9/1995 | Chambers et al. |
| 5,827,254 A | 10/1998 | Trombetta et al. |

(Continued)

FOREIGN PATENT DOCUMENTS

CN 1296399 A 5/2001

(Continued)

OTHER PUBLICATIONS

Examiner's Answer to Appeal Brief for Appeal No. 2008-004034 in Japanese Patent Application No. 2001-369516 mailed Oct. 27, 2009.

(Continued)

*Primary Examiner* — Jacqueline F. Stephens
(74) *Attorney, Agent, or Firm* — Birch, Stewart, Kolasch & Birch, LLP

(57) ABSTRACT

A disposable diaper comprising a liquid permeable topsheet 2, a liquid impermeable backsheet 3, and a liquid retentive absorbent member 4 and having a substantially oblong shape, the absorbent member 4 in the crotch portion having a middle absorbent portion 42 which occupies the middle 3/7 of the width of the absorbent member 4 and side absorbent portions 43 which each occupy the outermost 1/7 of the width of the absorbent member 4, wherein each side absorbent portion 43 has a larger unit absorption capacity than the middle absorbent portion 42, hydrophobic sheets 3 and 21 are disposed on the lateral outer edge of each side absorbent portion 43 to cover from the upper to lower surfaces of the edge, and an elastic member 71 is disposed in the part having each side absorbent portion 43 in the longitudinal direction of the side absorbent portion 43.

24 Claims, 16 Drawing Sheets

U.S. PATENT DOCUMENTS

| | | |
|---|---|---|
| 6,142,985 A | 11/2000 | Feist |
| 6,371,950 B1 | 4/2002 | Roslansky et al. |
| 6,498,283 B1 | 12/2002 | Wada et al. |
| 6,551,297 B2 | 4/2003 | Tanaka et al. |
| 6,595,976 B2 | 7/2003 | Jitoe et al. |
| 6,673,982 B1 | 1/2004 | Chen et al. |
| 6,793,649 B1 | 9/2004 | Fujioka et al. |
| 2002/0152540 A1 | 10/2002 | Van Gompel et al. |

FOREIGN PATENT DOCUMENTS

| | | |
|---|---|---|
| EP | 1-078-617 A2 | 2/2001 |
| JP | 59-190230 | 12/1984 |
| JP | 3-33622 U | 4/1991 |
| JP | 4-61523 U | 5/1992 |
| JP | 4-67427 U | 6/1992 |
| JP | 5-33630 B2 | 5/1993 |
| JP | 5-507865 A | 11/1993 |
| JP | 6-296643 A | 10/1994 |
| JP | 7-329 U | 1/1995 |
| JP | 8-280725 A | 10/1996 |
| JP | 9-075385 A | 3/1997 |
| JP | 9-506004 A | 6/1997 |
| JP | 9-173381 A | 7/1997 |
| JP | 9-313531 A | 12/1997 |
| JP | 11-019127 A | 1/1999 |
| JP | 11-128267 A | 5/1999 |
| JP | 11-332899 A | 12/1999 |
| JP | 2000-267 A | 1/2000 |
| JP | 3020989 B2 | 1/2000 |
| JP | 2000-166967 | 6/2000 |
| JP | 2000-201974 A | 7/2000 |
| JP | 3182040 B2 | 4/2001 |
| JP | 2001-137286 A | 5/2001 |
| JP | 2001-190581 A | 7/2001 |
| JP | 2001-299812 A | 10/2001 |
| JP | 2003-501213 A | 1/2003 |
| TW | 480181 | 3/2002 |
| WO | WO-91/19471 A1 | 12/1991 |
| WO | WO-9119471 A1 | 12/1991 |
| WO | WO-98/20916 | 5/1998 |
| WO | WO-99/51178 A1 | 10/1999 |
| WO | WO-00/76446 A1 | 12/2000 |

OTHER PUBLICATIONS

Japanese Application No. 2001-289941, Notice of Rejection, Oct. 12, 2010, 3 pages.

Japanese Application No. 2001-289941, Notice of Rejection, Feb. 8, 2011, pp. 1-3.

Longitudinal direction of the side absorbent portion

DISPOSABLE DIAPER

This application is a Divisional of application Ser. No. 10/466,692 filed on Jul. 21, 2003 now abandoned, which claims priority on PCT International Application No. PCT/JP02/09367 filed on Sep. 12, 2002, which claims priority on Japanese Application Nos. JP 2001-289941, JP 2001-346577, JP 2001-349620, JP 2001-369516, and JP 2001-380516 filed on Sep. 21, 2001, Nov. 12, 2001, Nov. 15, 2001, Dec. 4, 2001, and Dec. 13, 2001 respectively. The entire contents of each of these applications are hereby incorporated by reference.

BACKGROUND OF THE INVENTION

The present invention relates to a disposable diaper which can be produced at a lower cost and has greatly improved performance in leakproofness and fit.

The present invention relates to a disposable diaper which is used in combination with an auxiliary absorbent article, more particularly a disposable diaper having greatly improved performance in preventing leakage from the crotch and holding the auxiliary absorbent article.

The present invention relates to a disposable diaper excellent in fit to the inner side of wearer's thighs and leakproofness.

The present invention relates to a disposable diaper which securely bends at an expected position irrespective of slight variations in wearer's size or a diaperer's manner of diapering and thereby secures a desired fit and/or leakproofness.

The present invention relates to a disposable diaper in which the surface in contact with a wearer's body or a member disposed thereabouts, particularly an absorbent member greatly influential on the skin, hardly wrinkles or bunches up and therefore hardly causes skin troubles such as a bedsore.

In recent years, use of an auxiliary absorbent article such as a urine-absorbent pad in combination with a disposable diaper, particularly one for an adult has become frequent so as to alleviate the economical and physical burden of diapering.

However, conventional disposable diapers are not designed with due considerations for a combined use with an auxiliary absorbent article. There is another circumstance that leaks from the side and the crotch are frequent with those bedridden who often lie on their side for preventing decubial (bedsore) development.

When combined with a conventional disposable diaper, an auxiliary absorbent article can move while worn. If this occurs, the auxiliary absorbent article and/or the disposable diaper fail to efficiently exert their absorption capability, easily causing leakage from the crotch.

JP-B-5-33630 discloses a disposable diaper which has an absorbent member composed of a middle absorbent portion of a width fit to a human body and an outer absorbent portion disposed on each side of the middle absorbent portion and thereby provides an improved fit to the crotch and improved leakproofness. However, the disclosed disposable diaper has a disadvantage that, when a large amount of urine is discharged in a short time, urine leaking from the middle absorbent portion can flow over the outer absorbent portions relatively easily and leak out from around the thighs.

Japanese Patent 3020989 discloses a hydrophilic fiber absorbent element having a hydrogelling absorbent substance distributed in high concentration along both longitudinal side edges. The technique described in the patent resides in formation of a barrier by gel blocking so as to prevent liquid diffusion in the lateral direction. Its leakproofing mechanism is fundamentally different from that of the present invention.

A disposable diaper having a separate absorbent member disposed on both sides of an absorbent member in the crotch portion is known, in which the absorbent member on each side bends down while worn to conform to the inner side of a wearer's thigh. A disposable diaper of this type is capable of absorbing excretion that leaks laterally over the wearer's groins in the side portions thereof.

However, such a conventional disposable diaper has a poor fit to the inner side of the thighs so that excretion, such as urine and loose stools, that flows laterally over the groin can easily leak out from around the thigh without being absorbed by the side absorbent portion.

Also known is an absorbent article, such as a disposable diaper, having grooves formed by embossing, etc. on the absorbent member thereof so that the absorbent member may bend along the grooves for the purpose of, for example, improving leakproof performance. When actually put on a wearer, however, the absorbent member can often bend at a position other than the grooved positions, i.e., the positions where the absorbent member is expected to bend, because of variations of the wearer's size or the manner of diapering, and the like, resulting in a failure to provide a desired fit or leakproof performance. Where, in particular, a diaper has a wide absorbent member so that the longitudinal side portions of the absorbent member may come into contact with the wearer's thighs, the absorbent member is apt to bend at unexpected positions.

Further, disposable diapers, especially those for adults are liable to have their absorbent member wrinkled or bunched up in the portion disposed on the back side or the stomach side, particularly the back side, of a wearer. Body pressure application onto such wrinkled or bunched portions can cause skin troubles such as a bedsore.

JP-A-U-59-190230 discloses a sanitary napkin having a distinguishable colored sheet disposed on both sides of an absorbent member. U.S. Pat. No. 3,744,494 teaches a technique for preventing lateral liquid flow, in which parting lines are provided on an absorbent core to form barriers preventing a liquid flow.

SUMMARY OF THE INVENTION

A first object of the present invention is to provide a disposable diaper which can be produced at a lower cost and has greatly improved performance in leakproofness and fit.

A second object of the present invention is to provide a disposable diaper which has greatly improved performance in preventing leakage and holding an auxiliary absorbent article.

Another object of the present invention is to provide a disposable diaper which provides a good fit to the inner side of the thighs and has excellent leakproof performance.

Still another object of the present invention is to provide a disposable diaper, the absorbent member of which securely bends at an expected position in spite of variations of a wearer's size or manner of diapering thereby secures a desired fit and/or leakproof performance.

Yet another object of the present invention is to provide a disposable diaper in which the surface in contact with a wearer's body or a member disposed thereabouts, particularly an absorbent member greatly influential on the skin hardly wrinkles or bunches up and hardly causes skin troubles such as a bedsore.

In a first aspect of the present invention, there is provided a disposable diaper comprising a liquid permeable topsheet, a liquid impermeable backsheet, and a liquid retentive absorbent member and having a substantially oblong shape consisting of a back portion, a crotch portion and a stomach portion, wherein the absorbent member in the crotch portion has a middle absorbent portion which occupies 3/7 of the width of the absorbent member in the crotch portion and side absorbent portions which each occupy 1/7 of the width of the absorbent member in the crotch portion, wherein each of the side absorbent portions has a larger unit absorption capacity than the middle absorbent portion, one or two hydrophobic sheet(s) are disposed on the lateral outer edge of each of the side absorbent portions to cover from the upper to lower surfaces of the edge, and an elastic member is disposed in the part having each of the side absorbent portions in the longitudinal direction of the side absorbent portions.

In a second aspect of the present invention, there is provided a disposable diaper adapted to be used in combination with an auxiliary absorbent article placed on the inner side of the diaper, which comprises a liquid permeable topsheet, a liquid impermeable backsheet, and a liquid retentive absorbent member and having a substantially oblong shape consisting of a back portion, a crotch portion, and a stomach portion, the absorbent member in the crotch portion having a middle absorbent portion which occupies 1/3 of the width of the absorbent member in the crotch portion and side absorbent portions which each occupy 1/3 of the width of the absorbent member in the crotch portion, wherein each of the side absorbent portions has a higher maximum degree of swelling on absorption than the middle absorbent portion, and at least part of the inner surface of the part having each of the side absorbent portions comes into contact with a wearer's thigh while worn.

One or more of the objects of the invention are accomplished by a disposable diaper comprising a liquid permeable topsheet, a liquid impermeable backsheet, and a liquid retentive absorbent member and having a substantially oblong shape, wherein both side absorbent portions of the absorbent member in the crotch portion bend downward in conformity with the inner side of wearer's thighs while worn, and a plurality of compressed parts are formed on each of the side absorbent portions at intervals in the longitudinal direction of the side absorbent portions.

One or more of the objects of the invention are accomplished by a disposable diaper comprising a liquid permeable topsheet, a liquid impermeable backsheet, and a liquid retentive absorbent member and having a substantially oblong shape, wherein the absorbent member has a middle embossed portion, side embossed portions disposed on both sides of the middle embossed portion, and an intermediate portion disposed between the middle embossed portion and each of the side embossed portions, each of the middle and side embossed portions having the topsheet side thereof embossed and extending in the longitudinal direction of the diaper, and the absorbent member bends downward in the intermediate portion while worn.

The backsheet of a disposable diaper wrinkles by the friction with sheets, etc. when a wearer changes or is made to change his or her position, and the wrinkles of the backsheet influence the surface in contact with a wearer's skin or a member disposed thereabouts (e.g., the topsheet, the absorbent member) to cause the member to wile or bunch. The present inventors have considered this as the main cause of skin troubles and found that wrinkling or bunching of the absorbent member can be reduced to suppress development of skin troubles such as a bedsore by lowering the joint area ratio between the absorbent member and the backsheet in the back portion and/or the stomach portion than that in the crotch portion.

Accordingly, one or more objects of the present invention are accomplished by a disposable diaper comprising a liquid permeable topsheet, a liquid impermeable backsheet, and a liquid retentive absorbent member and having a substantially oblong shape consisting of a back portion, a crotch portion, and a stomach portion disposed in this order in the longitudinal direction, wherein the absorbent member and the backsheet are joined together, the area ratio of the joints between the absorbent member and the backsheet in each of the side portions having a prescribed width and extending in the longitudinal direction of the diaper is smaller in the back portion and the stomach portion than in the crotch portion, and an elastic member is disposed in its stretched state in the crotch portion of each of the side portions along the longitudinal direction of the diaper.

BRIEF DESCRIPTION OF THE DRAWINGS

The present invention will be more particularly described with reference to the accompanying drawings, in which.

DETAILED DESCRIPTION OF THE PREFERRED EMBODIMENTS

The present invention will be described in greater detail with reference to its preferred embodiments.

Figure 1:
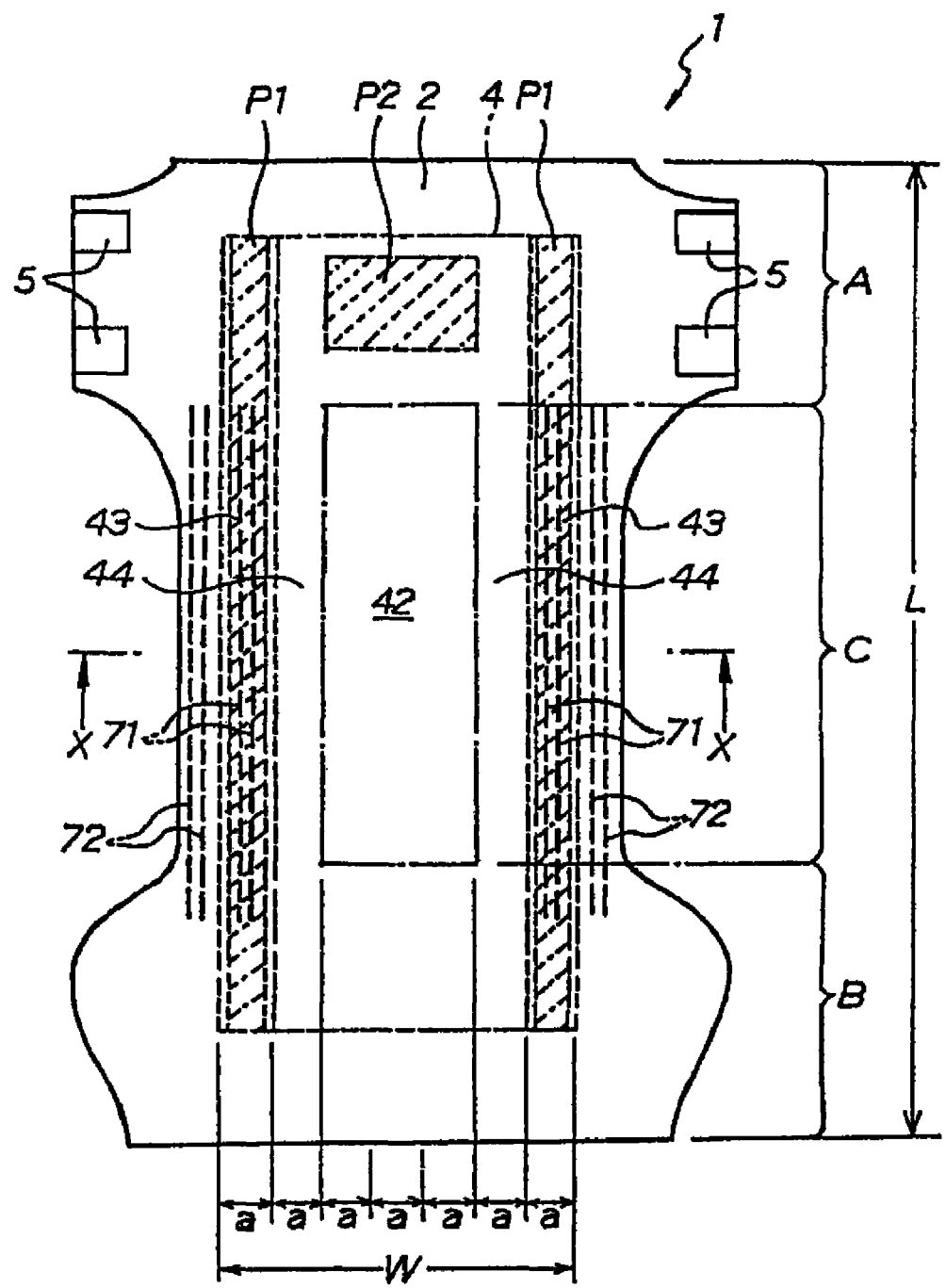
FIG. 1 is a plan view of an embodiment of the disposable diaper according to the first aspect of the invention.
Figure 2:
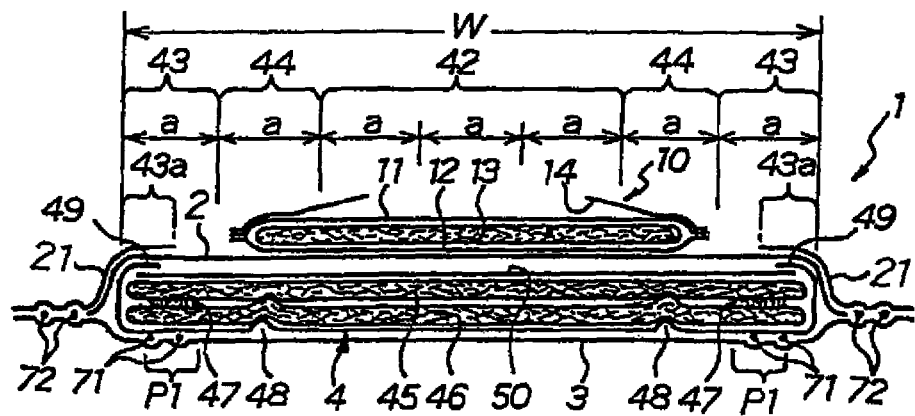
FIG. 2 is a schematic cross-section of FIG. 1, taken along line X-X.
Figure 3:
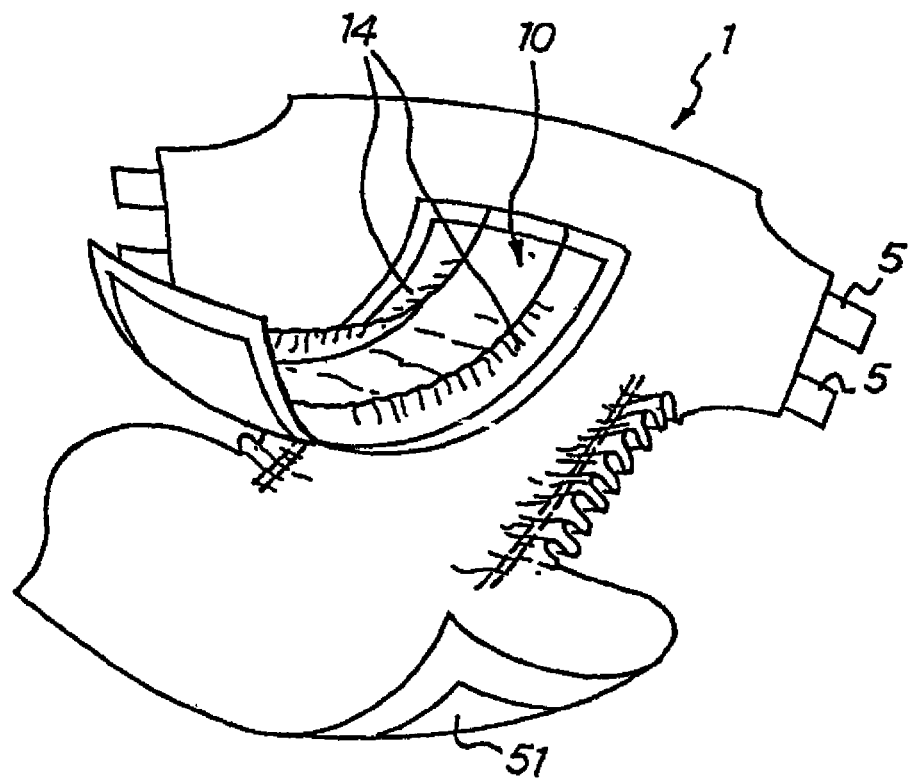
FIG. 3 is a perspective of the disposable diaper of FIG. 1 and an auxiliary absorbent article which is being laid on the inner side of the diaper.

FIGS. 1 through 3 show a disposable diaper 1 as an embodiment of the first aspect of the invention (hereinafter referred to as a first embodiment). The disposable diaper 1 of the first embodiment is of a flat or unfolded type having a substantially oblong shape. It comprises a liquid permeable topsheet 2, a liquid impermeable backsheet 3, and a liquid retentive absorbent member 4 interposed between the sheets 2 and 3. It has a back portion A which is to be disposed on the back side of a wearer, a stomach portion B which is to be disposed on the stomach side of a wearer, and a crotch portion C between the portions A and B. Fastening tapes 5 are provided on both lateral sides of the back portion A as a fastening means, and a landing zone 51 adapted to receive the fastening tapes 5 is provided on the outer side of the stomach portion B.

In detail, the disposable diaper 1 of the first embodiment has both side edges in the crotch portion C curved inward to make a sandglass shape. The absorbent member 4 is rectangular. The topsheet 2, which is rectangular, is laid on the inner side (wearer's side) of the absorbent member 4, and the backsheet 3, which is shaped to the outline of the diaper, is provided on the outer side (opposite to the wearer's side) of the absorbent member 4. The topsheet 2 slightly extends laterally outward from both sides of the absorbent member 4. A hydrophobic sheet 21 is laid bridging over the topsheet 2 and the backsheet 3 (the part of the backsheet 3 extending outward from the lateral edges of the absorbent member 4) and joined to each of them. The border between the topsheet 2 and the hydrophobic sheet 21 is not shown in FIG. 1.

In the first embodiment, the absorbent member 4 in the crotch portion C has a middle absorbent portion 42 which occupies the middle 3/7 of the width W (see FIGS. 1 and 2) of the absorbent member 4 in the crotch portion, side absorbent portions 43 which each occupy 1/7 of the width W, and intermediate portions 44 which are positioned between the middle absorbent portion 42 and each side absorbent portion 43 and each occupy 1/7 of the width W. Each side absorbent portion 43 has a larger unit absorption capacity than the middle absorbent portion 42.

Where the total length L of a disposable diaper in its stretched state (the state with elastic members hereinafter described are stretched out to make a diaper flat, hereinafter referred to as a flat-out state) is divided in equal quarters, the crotch portion C corresponds to the middle two quarters as shown in FIG. 1.

Figure 4:
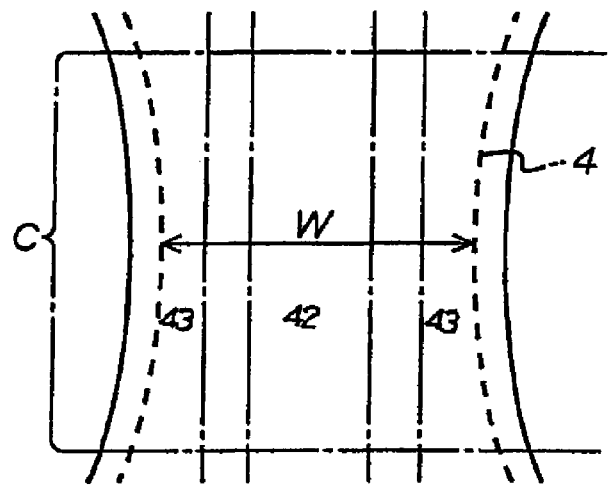
FIG. 4 is a plan of the crotch portion of another embodiment of the disposable diaper according to the first aspect of the invention.
Figure 8:
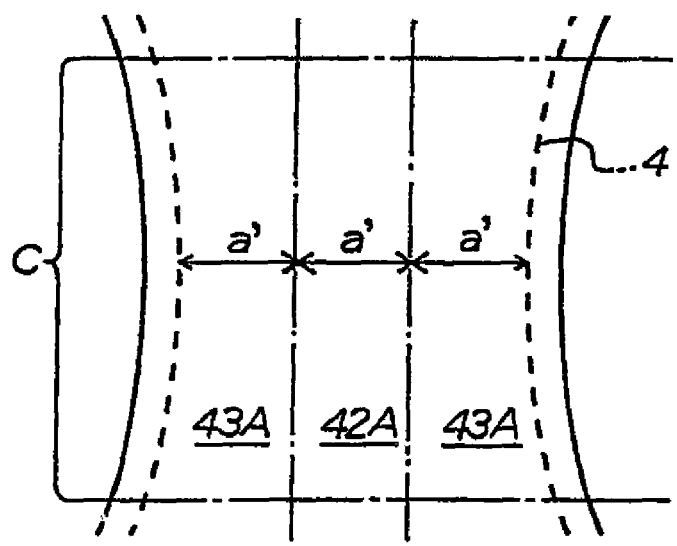
FIG. 8 is a plan of the crotch portion of another embodiment of the disposable diaper according to the second aspect of the invention.

The width W of the absorbent member 4 is the width in a flat-out state. Where the absorbent member 4 in the crotch portion C has a varied width along its length (such a case is shown in FIG. 4 and FIG. 8, in which both side edges of an absorbent member is curved inward so that the absorbent member is narrower in the middle part of the crotch portion than in the other parts nearer to the back portion B and the stomach portion A), the shortest distance between both side edges of the absorbent member in the crotch portion C is taken as the width W. Where a part of, or the whole of, an absorbent member is divided into separate sections, the outer lateral side edge of the crosswise outermost section is taken as the side edge of the absorbent member.

Since the middle absorbent portion 42 is a portion that is necessarily wetted by single urination, an auxiliary absorbent article 10 is usually placed on the middle absorbent portion 42. On the other hand, the side absorbent portions 43 are portions for absorbing liquid diffused out of the middle absorbent portion 42.

Accordingly, the side absorbent portions 43 are designed to have a larger unit absorption capacity than the middle absorbent portion 42. As a result, the absorbing capability of the absorbent member 4 is made efficient and full use of, which makes it possible to achieve improved leakproof performance even if the total absorption capacity of the absorbent member 4 is equal to or less than that of a conventional disposable diaper.

By relatively reducing the unit absorption capacity of the middle absorbent portion 42, the middle absorbent portion 42 is made to play a role in diffusing liquid especially in the longitudinal direction, instead of, or in addition to, a role in absorbing liquid. That is, the liquid flow speed is reduced by this diffusing action. It follows that the side absorbent portions are allowed to take time to absorb liquid. Further, since liquid is longitudinally diffused in the middle absorbent portion, a broad area of the side absorbent portions can be made effective use of. Thus further improvement on leakproof performance can be achieved while suppressing the production cost.

From the standpoint of production cost reduction and leakproofness improvement, the ratio of the unit absorption capacity of the middle absorbent portion 42 to that of the side absorbent portion 43 on each side is preferably in a range of from 0 to 0.9, particularly from 0 to 0.5. The difference of unit absorption capacity between them is preferably 0.1 to 0.8 g/cm$^2$, particularly 0.1 to 0.4 g/cm$^2$.

The unit absorption capacity of the side absorbent portions 43 preferably ranges from 0.1 to 0.8 g/cm$^2$, particularly 0.1 to 0.4 g/cm$^2$. To ensure slowdown of a liquid flow by liquid diffusion, it is preferred for the middle absorbent portion 42 to have a unit absorption capacity of 0 to 0.7 g/cm$^2$, particularly 0 to 0.2 g/cm$^2$.

To have the side absorbent portions absorb liquid efficiently, the unit absorption capacity of the intermediate portions 44, which are positioned between the middle absorbent portion 42 and each side absorbent portion 43, is preferably equal to or less than that of the middle absorbent portion 42. It is particularly preferred that the unit absorption capacity of the intermediate portions 44 be less than that of the middle absorbent portion 42. In this case, the liquid leaked from the auxiliary absorbent article is directly absorbed by the side absorbent portions 43 or, while longitudinally diffusing in the intermediate portions 44, absorbed by portions not having absorbed liquid, particularly the portions in each side absorbent portion that have not absorbed liquid. As a result, the side absorbent portions 43 are allowed to exhibit their absorptivity fully, thereby assuring highly efficient absorption.

The unit absorption capacity of the middle absorbent portion 42, the side absorbent portions 43, and the intermediate portions 44 is measured as follows. The area of each of the middle absorbent portion 42, the side absorbent portion 43, and the intermediate portion 44 is measured in the flat-out state of a diaper. Then the crotch portion C is cut out of the diaper. After removing the topsheet 2 and the backsheet 3, the crotch portion C is cut into the middle absorbent portion 42, the side absorbent portions 43, and the intermediate portions 44. Each cut piece is put into a mesh bag, the bag is closed, and the bag is immersed in 0.9 wt % physiological saline for 30 minutes, hung for 30 minutes for spontaneous drainage and dewatering, and centrifugally dried at 800 rpm for 10 minutes (radius of gyration: 200 mm). The unit absorption capacity of each portion is calculated from equation:

$$\text{Unit absorption capacity (g/cm}^2\text{)}=[(\text{weight (g) after drying})-(\text{weight (g) before immersion})]/\text{area (cm}^2\text{) of each portion}$$

The unit absorption capacity of the side absorbent portions 43 can be made higher than that of the middle absorbent portion 42 and/or the intermediate portions 44 by adjusting the respective basis weights, i.e., the weight of constituent materials, such as fibrous materials, e.g., pulp fiber and absorbent polymers, per unit area. It is preferred to adjust the respective basis weights by increasing the amount of an absorbent polymer in the side absorbent portions 43 over the other portions from the viewpoint of ease of obtaining desired effects and cost performance. It is preferred that the amount of an absorbent polymer be not so large as to cause gel blocking that can cause reduction of absorbing performance. In this connection an advisable average content of an absorbent polymer in the side absorbent portions 43 is 20 to 150 g/m$^2$, particularly 50 to 100 g/m$^2$. The average absorbent polymer content of each side absorbent portion 43 is obtained by dividing the weight of the absorbent polymer present in the side absorbent portion 43 by the area of that portion.

In the diaper 1 according to the first aspect of the invention, the outer side edge of each side absorbent portion 43 is covered with the hydrophobic sheets 3 and 21 from one side (the upper side or the wearer's side) to the other side (the lower side or the outer side) via the edge face, and an elastic member 71 is provided in the part having each side absorbent portion 43 along the longitudinal direction of that portion.

In the first embodiment, the elastic member 71 is provided at the back of the absorbent member (between the backsheet 3 and the sheet forming the outer surface of the absorbent member 4 in the embodiment shown in FIG. 2) in the part having each side absorbent portion 43, whereby the inner side of this part is securely brought into contact with the inner side of each thigh of a wearer to increase the probability of contact between the side absorbent portions 43 and excretion such as urine. Further, liquid that flows in the absorbent member without being absorbed by the side absorbent portions is prevented from leaking from the edges because the edges are covered with the hydrophobic sheets 3 and 21 and is in the meantime absorbed by the side absorbent portions 43.

The above-mentioned structure as well as the higher unit absorption capacity of the side absorbent portions 43 than that of the middle absorbent portion 42 make it possible to securely and effectively bring the absorbing performance of the side absorbent portions 43 to its best advantage and also to improve the leakproofness and the fit while holding down the production cost.

The term "fit" as referred to here is the fit of the side absorbent portions onto the inner side of the thighs in the crotch, thereby referring to a property of effectively preventing gaping that tends to occur between the side absorbent portions and the thighs when a diaper is put on a wearer or while a diaper is worn.

Figure 5:
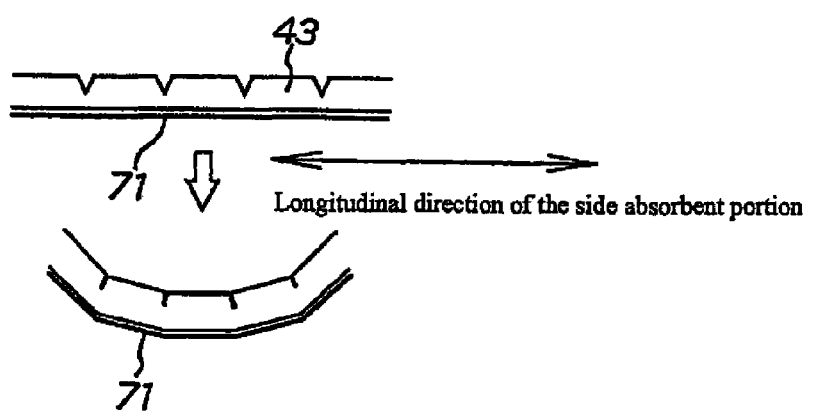
FIG. 5 is a partial longitudinal sectional view of a side absorbent portion of the absorbent member used in a preferred embodiment of the first and second aspects of the invention.

It is preferable for each of the side absorbent portions 43 of the diaper 1 according to the first embodiment or each of side absorbent portions 43A of a diaper 1' according to the second aspect of the invention hereinafter described to have two parts different in stiffness and almost parallel (at an angle of 0 to 45° C.) with the width direction of the side absorbent portions 43 (or 43A) arrayed alternately in the longitudinal direction of the side absorbent portions 43 (or 43A) as shown in FIG. 5 so that the side absorbent portions may smoothly be shirred or gathered in conformity to a wearer's body. Reduction of fit that may be caused by uneven gathering can thus be prevented. The parts different in stiffness are formed by, for example, (1) making parts from which the absorbent member is missing or parts with a reduced basis weight, (2) embossing to form fine linear depressions, (3) slitting, or (4) fabricating less stiff parts with a less stiff material than the material making the surroundings.

The elastic members 71 may be provided at any position in the thickness direction of the parts having the side absorbent portions 43 (or 43A), for example, between the topsheet 2 and the absorbent member 4 or in the back of the backsheet 3, as long as the parts may be securely brought into contact with wearer's thighs. For assuring a snug fit and alleviating irritation to the skin, the elastic members 71 are preferably disposed at the back of the absorbent member.

Figure 6:
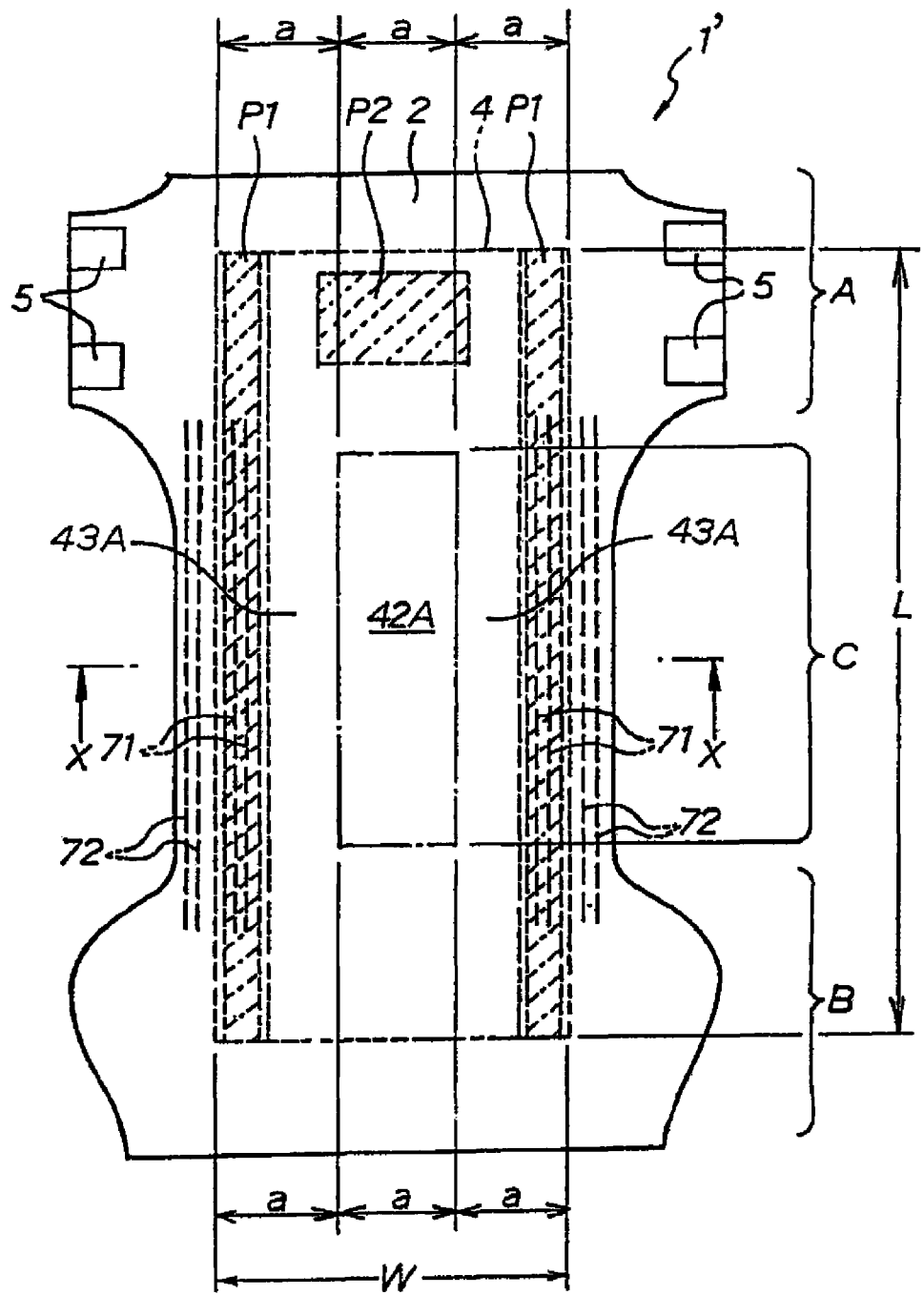
FIG. 6 is a plan of an embodiment of the disposable diaper according to the second aspect of the invention.
Figure 7:
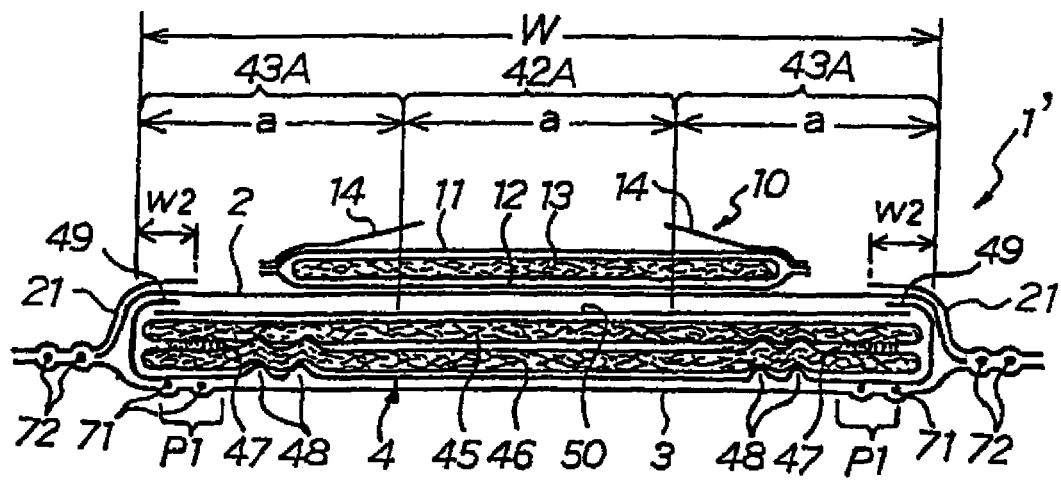
FIG. 7 is a schematic cross-section of FIG. 6, taken along line X-X.

As shown in FIGS. 1 and 6, the diaper 1 of the first embodiment and the diaper 1' described later have long and narrow polymer zones P1 in the side absorbent portions 43 (43A) along the longitudinal direction of the diaper and a rectangular polymer zone P2 in the absorbent member in the back portion A. As shown in FIGS. 2 and 7, these polymer zones P1 and P2 are made of an absorbent polymer 47 disposed between an upper fiber layer 45 and a lower fiber layer 46 each fabricated of fibrous materials such as pulp fiber. The absorbent member of these embodiments contains no absorbent polymer in other areas than the polymer zones P1 and P2.

In the first embodiment, the part 43a of each side absorbent portion 43 which is covered with the hydrophobic sheets 21 and 3 on the upper and the lower sides thereof has a smaller average absorbent polymer content than the average absorbent polymer content of the whole side absorbent portion 43. Thus, a liquid flowing laterally in the side absorbent portions 43 without being absorbed moves and diffuses longitudinally within the part 43a covered with the hydrophobic sheets 3 and 21 and is efficiently absorbed by the absorbent polymer in the part not having absorbed liquid.

In order to facilitate efficient diffusion and absorption, it is preferred that the part 43a covered with the hydrophobic sheets 3 and 21 have an average absorbent polymer content of 0 to 120 g/m$^2$, particularly 0 to 60 g/m$^2$; that the ratio of the average absorbent polymer content of the part 43a to that of the whole side absorbent portion 43 be 0 to 0.6, particularly 0 to 0.4; and that the difference between the average absorbent polymer content of the part 43a and that of the whole side absorbent portion 43 be 20 to 150 g/m$^2$, particularly 30 to 100 g/m$^2$. The average absorbent polymer content of the part 43a covered with the hydrophobic sheets 3 and 21 is obtained by dividing the weight of the polymer in the part 43a by the area of the part 43a. The average absorbent polymer content of the middle absorbent portion 42, which is obtained by dividing the polymer weight in the middle absorbent portion 42 by the area of the portion 42, is preferably 0 to 100 g/m$^2$, particularly 0 to 50 g/m$^2$. A preferred average absorbent polymer content of the side absorbent portion 43 is as stated above.

The width of the part 43a covered with the hydrophobic sheets 3 and 21 (the width of the overlap of the sheet 21 on the absorbent member 4) is preferably 5 to 30 mm, still preferably 5 to 15 mm. With a 5 mm or larger width, leakage from the edge of the absorbent member can be prevented without fail. With a 30 mm or smaller width, a sufficient width of the hydrophilic area (absorbent member) is secured to exhibit sufficient leakproofness against liquid flowing on the surface. In the first embodiment, the upper surface of each side edge of the absorbent member 4 is covered with the sheet 21 over the whole length of the absorbent member with the same width of the overlap. The hydrophobic (liquid impermeable) sheets 3 (backsheet) and 21 are joined together liquid-tight in their extensions from each edge of the absorbent member 4.

The thickness of the middle absorbent portion 42 is preferably ⅔ or smaller of that of each side absorbent portion 43. With this thickness there is formed concavity in the middle of the diaper, which would help an auxiliary absorbent article, if placed, to be held in and to be prevented from moving. Where the middle absorbent portion 42 and each side absorbent portion 43 have equal densities, the smaller thickness of the middle absorbent portion will bring improved breathability. Particularly where the backsheet 3 is moisture permeable, overhydration and rashes will be greatly reduced as compared with the middle absorbent portion 42 having the same thickness as the side absorbent portions 43.

In order to secure the capabilities of holding an auxiliary absorbent article and preventing it from moving, the thickness of the middle absorbent portion 42 is still preferably a half of or smaller than that of the side absorbent portions 43, particularly preferably zero.

The thickness of the middle absorbent portion 42 and each side absorbent portion 43 is measured as follows. An absorbent member 4 is taken out of an unused disposable diaper. The thickness of each of the middle absorbent portion 42 and the side absorbent portion 43 is measured at arbitrarily selected three points (preferably each selected from each of 5 cm squares continuous in the longitudinal direction in the crotch portion) under a load of 20 g/cm$^2$, and the average of the three points is calculated. Where there is no absorbent member, the thickness is taken as 0.

From the viewpoint of diaper shape retention, the absorbent member 4 in the crotch portion is preferably hollowed out in its crosswise middle part (e.g., the middle absorbent portion 42) to leave a frame. In this case, the topsheet 2 and the backsheet 3 in the hollow part are preferably joined together either directly or indirectly to securely form concavity in which an auxiliary absorbent article is held and prevented from moving.

For preventing an auxiliary absorbent article put on the absorbent member from sliding forward or backward, it is also preferred that the absorbent member 4 in the crotch portion be thinner in its crosswise middle part (e.g., the middle absorbent portion 42) than in the surroundings. The middle absorbent portion 42 can be hollow by removing part of the absorbent member.

A low stiff part 48 is formed in each intermediate portion 44 of the first embodiment in the longitudinal direction for helping the intermediate portions 44 bend downward (toward the backsheet side) while worn. Even where a diaper is designed to have a fairly wide absorbent member 4, the intermediate portions 44 are bent at the low stiff parts 48 to securely bring the side absorbent portions 43 into contact with wearer's thighs thereby preventing reduction of absorbing performance which may result from deformation of the diaper or an incorrect manner of diapering.

The low stiff parts are not restricted by the configuration or the method of formation as far as they help the intermediate portions bend easily. For example, the low stiff parts can be formed by (1) making parts from which an absorbent member is missing or parts with a reduced basis weight, (2) embossing to make fine linear depressions, (3) slitting, or (4) fabricating less stiff parts with a less stiff material than the surrounding material.

The diaper 1 of the first embodiment and the diaper 1' described later has, near each crosswise edge of the absorbent member 4 in the crotch portion C, an indicator 49 which is visually distinguishable when viewed from the inner side of the diaper. In the embodiments shown in FIGS. 2 and 7, color paper (e.g., yellowish green paper) covering the back side of the absorbent member 4 is folded back inward at both edges of the absorbent member 4 to serve as the indicators 49.

The indicators 49 near the edges of the absorbent member 4 make the crosswise middle portion of the absorbent member 4 outstanding, helping a diaperer to easily recognize where to place an auxiliary absorbent article correctly in rediapering. Thus, the effects of the present invention can be produced more securely and more efficiently.

The indicators can be of materials different from the materials disposed in the crosswise middle portion of the absorbent member (e.g., the topsheet 2, liquid impermeable paper or nonwoven fabric 50 covering the inner side of the absorbent member 4, etc.) in (1) color (e.g., non-white colored paper or nonwoven fabric), (2) pattern, (3) thickness, and the like.

The auxiliary absorbent article 10 shown in FIGS. 2, 3, 7, 9(*a*), and 9(*b*) comprises a liquid permeable topsheet 11, a liquid impermeable backsheet 12, and a liquid retentive absorbent member 13 interposed between these sheets and has upstanding gathers 14 on both lateral sides. It is adapted to be superposed on a diaper with its longitudinal direction agreeing with the longitudinal direction of the diaper.

The disposable diaper 1' which is one embodiment according to the second aspect of the present invention (hereinafter referred to as a second embodiment) is then described. The diaper 1' will be illustrated chiefly with reference to differences from the first embodiment. The same elements as in the first embodiment are given the same reference numerals as used in the first embodiment, with description therefor omitted.

In the disposable diaper 1', the absorbent member 4 in the crotch portion C has a middle absorbent portion 42A which occupies the middle ⅓ of the width W of the absorbent member in the crotch portion (see FIGS. 6 and 7) and side absorbent portions 43A each occupying ⅓ of the width W (the portions adjoining both sides of the middle absorbent portion 42A). The maximum degree of swelling on absorption (hereinafter simply referred to as a "maximum swelling degree") of each side absorbent portion 43A is greater than that of the middle absorbent portion 42A. Further, the absorbent member 4 is designed so that at least part of the inner surface of the part having each side absorbent portion 43A in the thickness direction may come into contact with a wearer's thigh while worn.

Figure 9A:
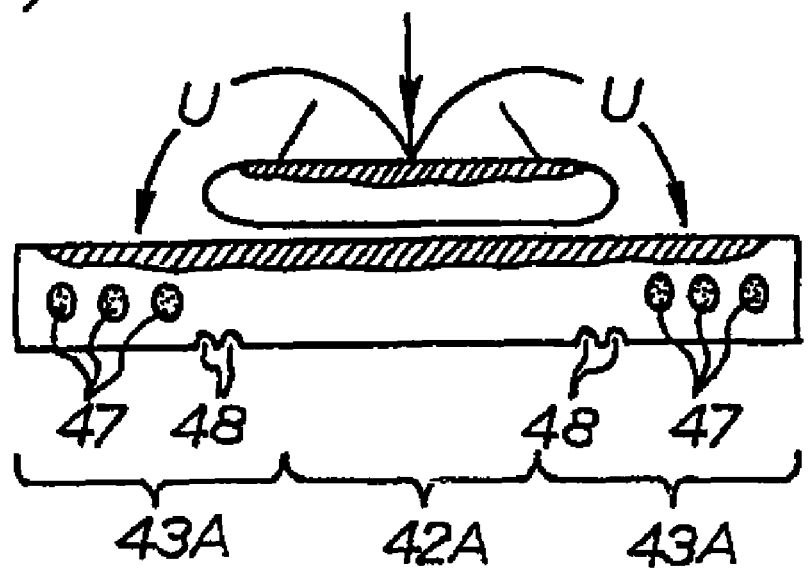
FIG. 9 schematically illustrates the action and effect of the second aspect of the invention.
Figure 9B:
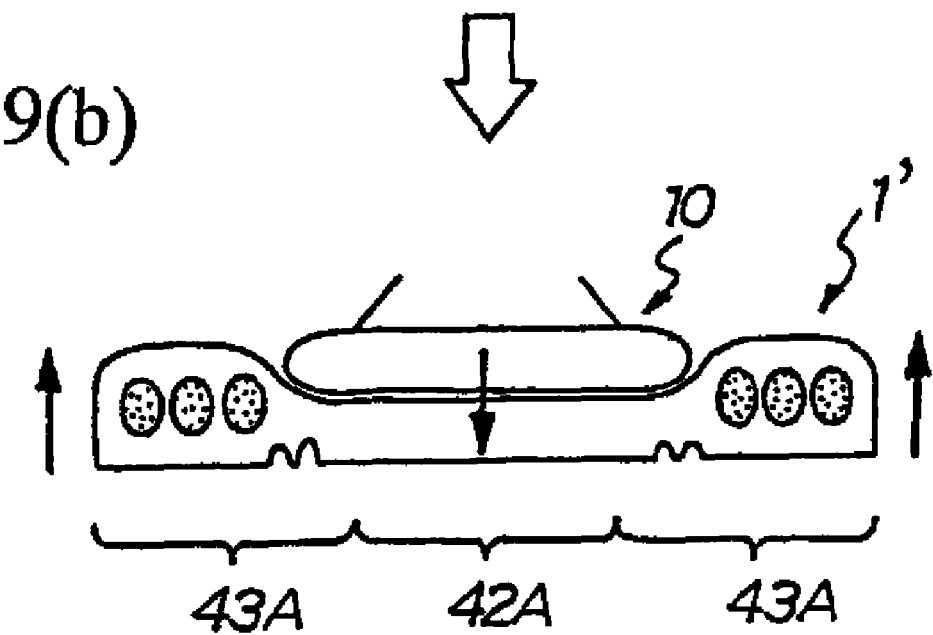

Since the side absorbent portions 43A show a higher maximum swelling degree that the middle absorbent portion 42A, when liquid U flows over from the auxiliary absorbent article 10 and is absorbed by the side absorbent portions 43A as shown in FIG. 9(*a*), the side absorbent portions 43A rise and gain in thickness as shown in FIG. 9(*b*) to exert an increased pressure onto the thighs thereby effectively preventing leakage from the crotch. At the same time, rising of the side absorbent portions 43A makes a depression in the area having the middle absorbent portion 42A, in which the auxiliary absorbent article can be held more securely and prevented from moving while worn.

While worn, the disposable diaper 1' brings a crosswise part or the crosswise whole of the areas having the side absorbent portions 43A into contact with wearer's thighs. In order to prevent a leak from around wearer's thighs, the part of the area having each side absorbent portion 43A which comes into contact with a wearer's thigh is preferably at least ⅕, still preferably at least ⅓, of the width of each side absorbent portion 43A, and this part should have an absorbent polymer disposed therein.

Each side absorbent portion 43A preferably has a maximum swelling degree A higher than 1.1, and the middle absorbent portion 42A preferably has a maximum swelling degree B lower than 1.0. It is particularly preferred for obtaining the above effects more appreciably that the maximum swelling degree A be higher than 1.5 and that the maximum swelling degree B be lower than 0.9.

For the middle absorbent portion 42A to have a maximum swelling degree B lower than 1.0 means that, when urine U flows over from the auxiliary absorbent article 10 and into the middle absorbent portion 42A, the middle absorbent portion 42A reduces its thickness to deepen the depression in which the auxiliary absorbent article 10 is retained. As a result, the auxiliary absorbent article 10 is held more firmly, and discomfort that may have been caused by the swollen auxiliary absorbent article's pressing the wearer's body is not or little felt.

The side absorbent portion 43A which has a maximum swelling degree A higher than 1.1 rises on absorbing urine and comes into intimate contact with a wearer's thigh to effectively prevent a leak from the crotch. To prevent skin troubles which may be caused by the intimate contact of the urine-containing absorbent member with the skin, it is advisable to take a measure against liquid backflow (for example, an auxiliary layer made of a backflow preventive material can be provided on the absorbent member) or a skin protective measure (for example, an antimicrobial material can be used).

For securing leakproof performance and auxiliary absorbent article-holding capability, the ratio of the maximum swelling degree B of the middle absorbent portion 42A to the maximum swelling degree A of the side absorbent portions 43A is preferably 0.2 to 0.9, still preferably 0.4 to 0.6, and the difference between them (A-B) is preferably 0.2 to 2.4, still preferably 0.6 to 1.1.

The maximum swelling degree of the middle absorbent portion 42A and the side absorbent portions 43A is measured as follows. An absorbent member 4 is taken out of an unused disposable diaper. The thickness of each of the middle absorbent portion 42A and the side absorbent portion 43A is measured at arbitrarily selected three points (preferably each selected from each of 5 cm squares continuous in the longitudinal direction in the crotch portion) under a load of 20 g/cm². Then, with no load applied, the entire area of the absorbent member is uniformly sprinkled with 0.5 g/cm² of 0.9 wt % physiological saline. After 10 minutes standing, the thickness of the absorbent member is again measured at the same measuring points under a load of 20 g/cm². The swelling degree at each measuring point for each absorbent portion is obtained by dividing the thickness after absorption by the thickness before absorption.

The highest value of the three points for each absorbent portion is taken as the maximum swelling degree of that portion.

The maximum swelling degree of the side absorbent portions 43A can be made higher than that of the middle absorbent portion 42A by, for example, (1) increasing the weight of a constituent material(s) of the side absorbent portions 43A (e.g., fibrous materials such as pulp fiber and/or an absorbent polymer) per unit area over that of the middle absorbent portion 42A or (2) fabricating the side absorbent portions of materials (e.g., fibrous materials such as pulp fiber and/or an absorbent polymer) showing higher rates of volume increase on liquid absorption than the materials fabricating the middle absorbent portion.

Of these methods, a method by increasing the highest absorbent polymer content of the side absorbent portions 43A over that of the middle absorbent portion 42A is preferred for improving leakproof performance and auxiliary absorbent article-holding performance and for ease of controlling the maximum swelling degrees. The term "highest absorbent polymer content" as used herein refers to the highest of the absorbent polymer contents measured in a 10 mm wide and 50 mm long area of each absorbent portion with the width and length directions agreeing with the width and length directions of the absorbent member. The highest absorbent polymer content of the middle absorbent portion 42A is preferably 0 to 100 g/m², still preferably 0 to 50 g/m², and that of the side absorbent portions 43A is preferably 50 to 200 g/m², still preferably 100 to 150 g/m². The ratio of the highest polymer content of the middle absorbent portion 42A to that of the side absorbent portions 43A is preferably 0 to 0.8, still preferably 0 to 0.5.

An elastic member 71 is provided in the part having each side absorbent portion 43A along the longitudinal direction of the portion 43A. In the second embodiment, the elastic member 71 is provided at the back of the absorbent member (between the backsheet 3 and the sheet forming the outer surface of the absorbent member 4). By disposing the elastic member 71 in the parts having the side absorbent portion 43A, the inner side of these parts is securely brought into contact with the thighs of a wearer to further improve the leakproof performance. While the elastic members 71 may be provided at any position in the thickness direction of the parts having the side absorbent portions 43A (for example, between the topsheet 2 and the absorbent member 4), it is preferably provided in the back of the absorbent member 4 as shown in FIG. 7 for facilitating bending of the side absorbent portions 43A and alleviating irritation to the skin.

For further improving the leakproof performance, both lateral sides of the topsheet 2 are preferably covered with respective hydrophobic sheets 21. It is more preferred that both lateral sides of the topsheet 2 and both lateral sides of the absorbent member 4 be covered with the hydrophobic sheets 21. The width of the overlap of the sheet 21 on each side of the absorbent member 4 (W2, see FIG. 7) is preferably 5 to 30 mm, still preferably 5 to 15 mm.

A low stiff part 48 is formed in each side absorbent portion 43A in the longitudinal direction for helping the side absorbent portions 43A bend downward (toward the backsheet side) while worn. The side absorbent portions 43A bend at the low stiff parts 48 to securely bring the inner side of the absorbent portions 43A into contact with wearer's thighs thereby preventing reduction of absorbing performance that might be caused by deformation of the diaper or an incorrect manner of diapering.

The number of the low stiff parts 48 per side absorbent portion offers as many bending axes around which the side absorbent portion easily bends in conformity to a wearer's body. It is preferred to make 2 to 5 low stiff parts per side absorbent portion.

The low stiff parts are not restricted by the configuration or the method of formation as far as they make the side absorbent portions bend easily. For example, the low stiff parts can be formed by (1) making parts from which an absorbent member is missing or parts with a reduced basis weight, (2) embossing to make fine linear depressions, (3) slitting, or (4) fabricating the parts with a less stiff material than the surrounding material.

In the disposable diaper 1' according to the second embodiment, the areas having the side absorbent portion 43A or in the vicinities of the areas have no elastic member above the topsheet 2. If an elastic member as has been often used in disposable diapers (e.g., natural rubber, synthetic rubbers, e.g., styrene-butadiene rubber, isoprene rubber, and neoprene rubber, EVA, extensible polyolefin, and polyurethane) is disposed above the topsheet in the above-described areas, the elastic members would exert a contracting force to cause the side absorbent portions 43A facing the thighs to form concavity thereby separating from the thighs and reducing the contacting force. Such a disadvantage can be eliminated by not using elastic members in the above-described position.

Disposable diapers 1A, 1B, and 1C according to other embodiments of the present invention will then be described. One or more elements possessed by the disposable diapers 1A, 1B, and 1C are applicable to the above-described diaper 1 or 1'.

Figure 10:
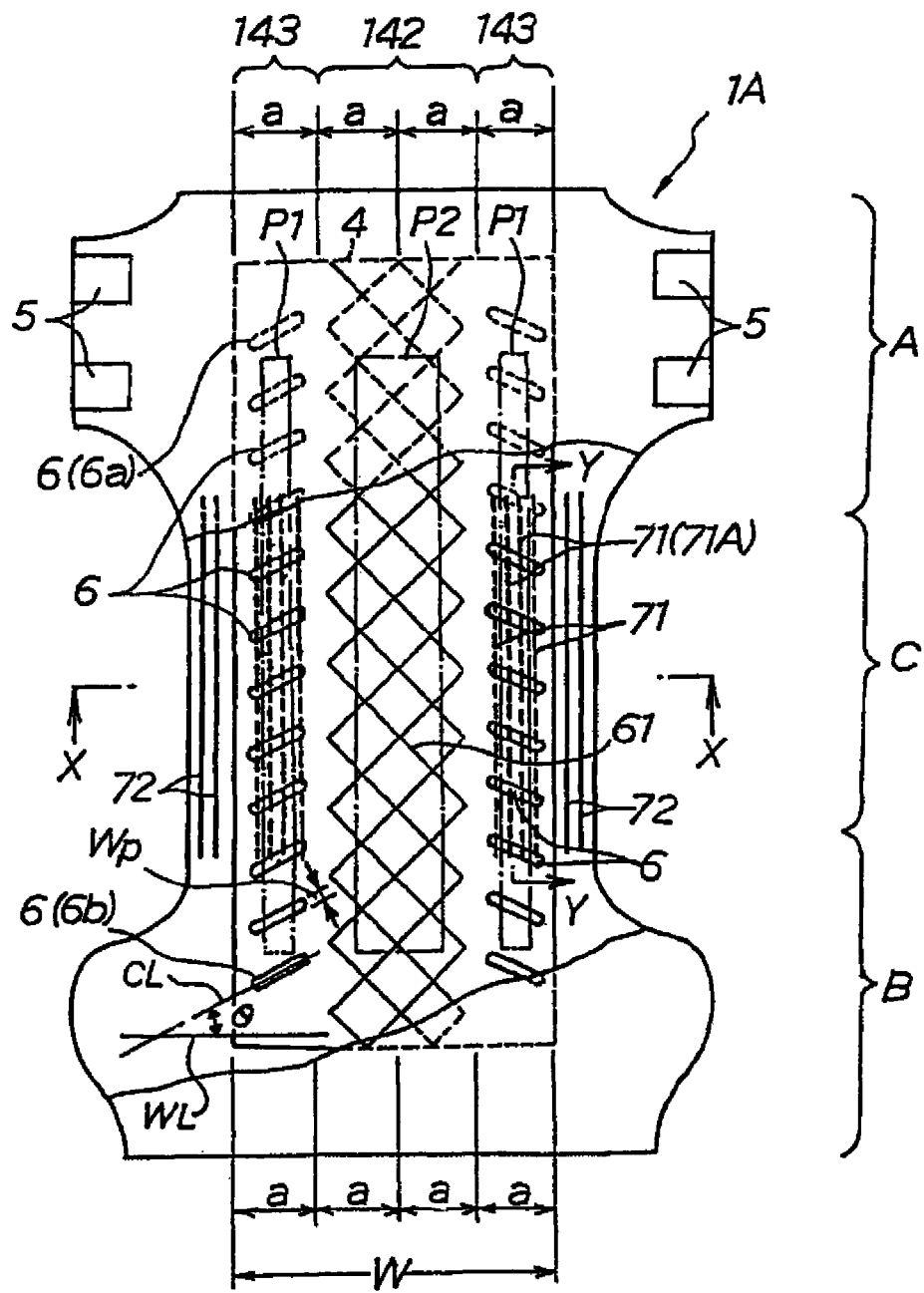
FIG. 10 is a plan of another embodiment of the disposable diaper according to the invention with a part cut away.
Figure 11:
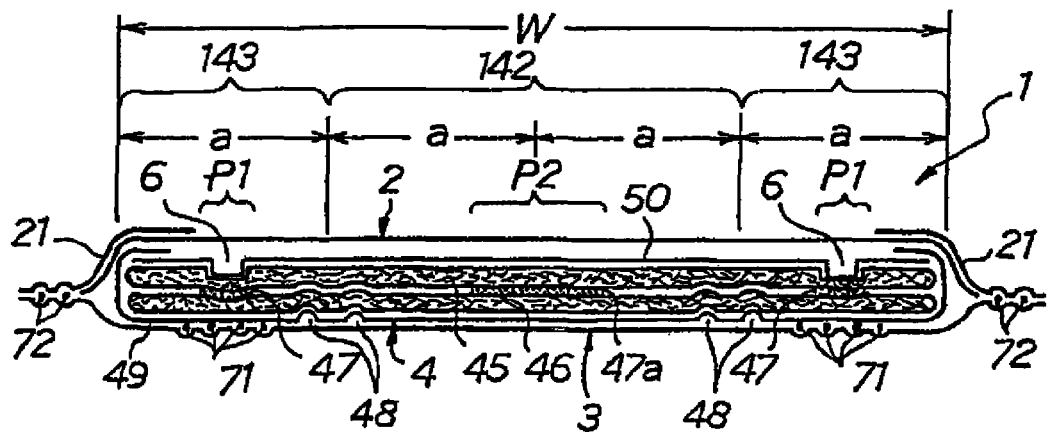
FIG. 11 is a schematic cross-section of the disposable diaper of FIG. 10, taken along line X-X.
Figure 12:
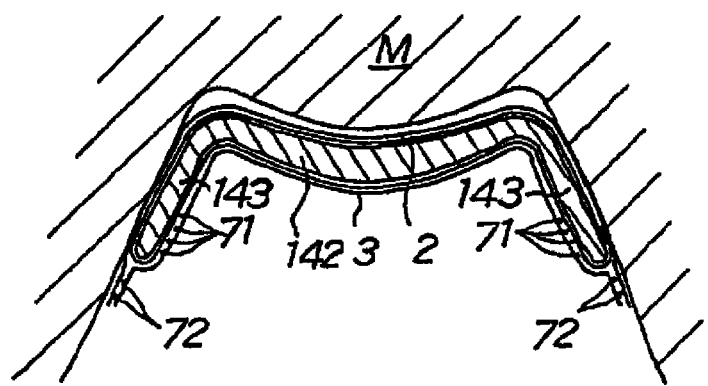
FIG. 12 is a schematic cross-section of the crotch portion of the disposable diaper of FIG. 10 while worn.

The disposable diaper 1A shown in FIGS. 10 and 11 is designed so that side portions 143 of the absorbent member 4 in the crotch portion C may bend downward in conformity with the inner side of wearer M's thighs while worn as illustrated in FIG. 12.

The side absorbent portions 143 which bend in conformity with the wearer's thighs correspond to the right and the left side absorbent portions each occupying about ¼ of the width W (see FIGS. 10 and 11) of the absorbent member 4 in the crotch portion C.

A plurality of compressed parts 6 are formed in each side portion 143 at intervals in the longitudinal direction of the side portions. The compressed parts 6 formed in the side portions 143 not only prevent the side portions 143 from getting wavy in parts but help the side portions 143 curve smoothly along the contour of a wearer's body.

Without the compressed parts 6, the side portions are liable to sag or wave in parts. With the compressed parts 6, the areas having the side portions 143 (hereinafter also referred to as side absorbent portions) provide a snug fit to the inner side of wearer's thighs under a uniform contact pressure thereby giving a wearer comfort. Further, with no gap formed between the side absorbent portions and the thighs, urine, etc. flowing over the groins is absorbed by the side absorbent parts without failing to exhibit excellent leakproof performance.

Figure 13A:
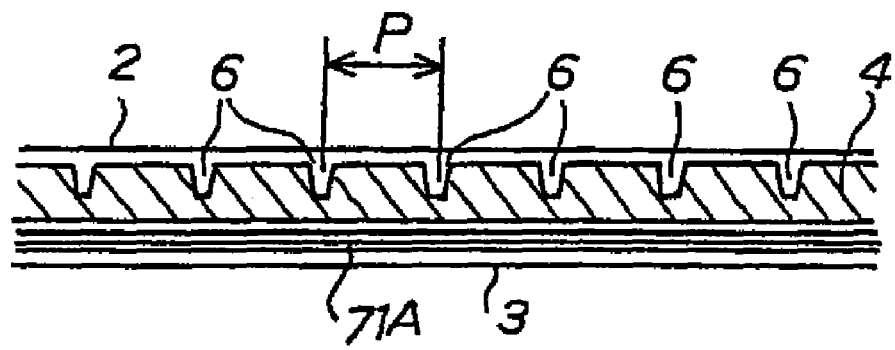
FIGS. 13(a) and 13(b) are each a schematic partial longitudinal section of the disposable diaper of FIG. 10, taken along line Y-Y, in a flat-out state and in a state while worn, respectively.

The compressed parts 6 each have a narrow, oblong elliptical shape whose longitudinal direction almost coincides with the width direction of the side portions 143. Referring to FIG. 10, the angle θ formed between the longitudinal direction of each compressed part 6 (indicated by centerline CL) and the width direction of the diaper 1A (indicated by line WL) is preferably 0 to 45°, still preferably 0 to 30°, from the standpoint of an improved fit. From the same standpoint, the width Wp of each compressed part 6 is preferably 0.5 to 15 mm, still preferably 1 to 5 mm, and the pitch P (see FIG. 13(a)) is preferably 3 to 35 mm, still preferably 5 to 20 mm. Where the centerline CL of the compressed part 6 is slanted, it is preferred for a good fit to thighs that the compressed part 6 is slanted upward (toward the back portion A) to the crosswise middle of the diaper.

An elastic member 71 is provided in its stretched state in the part having each side portion 143 (side absorbent portion) across a plurality of the compressed parts 6. The elastic members 71 across the compressed parts 6 contract to bring the side absorbent portions into intimate contact with the inner side of the thighs of a wearer and also regulate gathering of the side absorbent portions on contraction to prevent irregular sagging or waving of the side portions 143. With the regularly gathered side absorbent portions pressed onto the inner side of the thighs, leakage from the crotch is prevented more securely. Where the side absorbent portions contain an absorbent polymer as described later, the contact pressure of the side absorbent portions toward the thighs is increased by swelling of the absorbent polymer with urine to further improve leakproof performance.

Figure 13B:
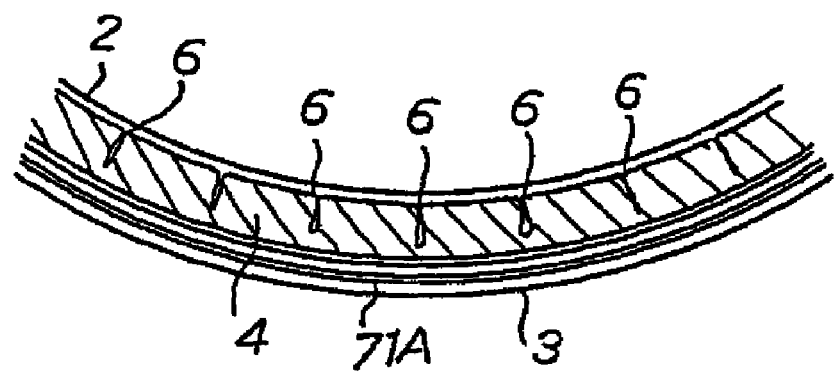

The compressed parts 6 are formed by pressing the absorbent member 4 by embossing from its topsheet 2 side (wearer's side). That is, the compressed parts 6 are formed by pressing the absorbent member from the topsheet 2 side of the absorbent member 4, which is the inner side of each side absorbent portion curved along the curve of a thigh while worn, to form depressions on that side. The depressions on the inner side of the curve her improve the fit of the side absorbent portions to the thighs. While the diaper is worn, the depressions on the topsheet 2 side are closed as shown in FIG. 13(b), which further levels the contact pressure to the thighs to provide a further improved fit and leakproofness.

The compression by embossing does not cause reduction of absorbing performance because the embossed pattern disappears on getting wet with liquid and does not hinder the absorbent member in swelling.

As shown in FIG. 11, each side portion 143 has a laminate structure composed of a plurality of absorbent layers including an upper fiber layer 45 and a lower fiber layer 46. An absorbent polymer 47 is provided in each side portion 143 between the upper fiber layer 45 and the lower fiber layer 46 to form a long and narrow polymer zone P1, which extends over the crotch portion C in the longitudinal direction of the diaper.

As shown in FIG. 10, at least one of, preferably more than one of; the compressed parts 6 are formed in each area where the polymer zone P1 lies. Further, at least one compressed part 6a (6b is formed out of each longitudinal end of each polymer zone P1. The upper and lower fiber layers 45 and 46 are made of fibrous materials, such as pulp fiber and hydrophilic synthetic fibers, and the absorbent polymer 47 is held therebetween.

By providing the polymer zone P1 in each side portion 143, especially in the area having the elastic member 71A provided, leaks from the crotch are prevented more securely.

It is preferred to provide both compressed parts 6 (in the area where the polymer zone P1 exists) and compressed parts 6a, 6b (in the area out of each longitudinal end of each polymer zone P1) for the following reason. The longitudinal ends of the absorbent member are to be disposed on the back and the stomach of a wearer. If these parts are hard, they will strongly irritate the skin of a wearer, especially an aged person confined to a bed, to cause scratches or bleeding. Therefore, it is unfavorable to fix the polymer with an adhesive. According to this structure, the absorbent polymer 47 is prevented from leaking. In addition, partially compressing the polymer zone P1 imparts moderate hardness to the side portions 143, which is effective to prevent the side portions 143 from bunching up.

To prevent leakage of the absorbent polymer 47, the compressed parts 6 are preferably formed across the polymer zone P1.

The crosswise middle portion 142 of the absorbent member 4 which is positioned between the side portions 143 also has a compressed part 61 formed by embossing in a lattice pattern which is different from the embossing pattern on the side portions 143. As a result, the middle portion 142 looks different from the side portions 143. This helps a diaperer recognize where to place an auxiliary absorbent article, if used in combination, while minimizing an increase of cost.

Similarly to the side portions 143, the middle portion 142 also contains an absorbent polymer 47a in its crosswise middle to form a rectangular polymer zone P2.

The absorbent member 4 has a laminate structure composed of an upper fiber layer 45 and a lower fiber layer 46, each having a rectangular shape in their plan view, and the absorbent polymer layers 47 and 47a sandwiched in these fiber layers. The laminate structure is wrapped in between two liquid permeable sheets 49 and 50. In FIG. 11, the illustration of the compressed part 61 is omitted.

The absorbent member 4 of the diaper 1A preferably has a bending axis 48 on the boundary between each side portion 143 and the middle portion 142. The bending axis 48 facilitates the absorbent member's bending downward so as to securely bring the inner side of the areas having each side portion 143 (side absorbent portion) into contact with the inner side of the wearer's thighs. The bending axis 48 is not restricted by the configuration or method of formation as far as it facilitates the absorbent member 4's bending downward. For example, the bending axis can be formed by (1) making a part from which an absorbent member is missing or a part with a reduced basis weight in the longitudinal direction, (2) embossing to make a fine linear depression in the longitudinal direction, (3) slitting in the longitudinal direction, or (4) fabricating a part of the absorbent member with a less stiff material than the surrounding material.

According to the embodiment shown in FIG. 10, the disposable diaper 1A has two fine linear depressions 48 formed by embossing as two bending axes on each boundary between each side portion 143 and the middle portion 142. The diaper 1A also has a second elastic member 72 extending in the longitudinal direction of the diaper within the crotch portion C at a position out of each lateral edge of the absorbent member 4 so that the parts having the elastic member 72 may come into close contact with the wearer's thighs.

An elastic member may be provided at the parts where the bending axes 48 exist to press the parts onto the wearer's groins while taking case not to cause the crosswise middle portion to bunch up and reduce ease of diapering.

The shape and arrangement of the compressed parts 6 in the diaper 1A are subject to variation. The elastic members 71 may be provided at any position in the thickness direction of the parts having the side portions 143, for example, between the topsheet 2 and the absorbent member 4 or on the back surface of the backsheet 3 as far as the parts having the side portions 143 are securely brought into contact with wearer's thighs.

The inner surface (the surface coming into contact with a wearer) of the disposable diaper may be formed solely of the topsheet 2.

An indicator which is visually distinguishable when viewed from the inner side of the diaper may be provided near each lateral edge of the absorbent member 4 in the crotch portion C. For example, color paper (e.g., yellowish green paper) can be used as a sheet 49, which covers the lower side of the absorbent member 4 and is folded back inward at both edges of the absorbent member 4, to serve as the indicator. This manipulation may be adopted in place of, or in addition to, the above-mentioned embossing in different patterns between the middle portion and each side portions.

The width of the side portions 143 is not limited to ¼ of the total width of the absorbent member 4 and is subject to alteration according to the wearer's size, the situation of diapering, and the like.

Figure 14:
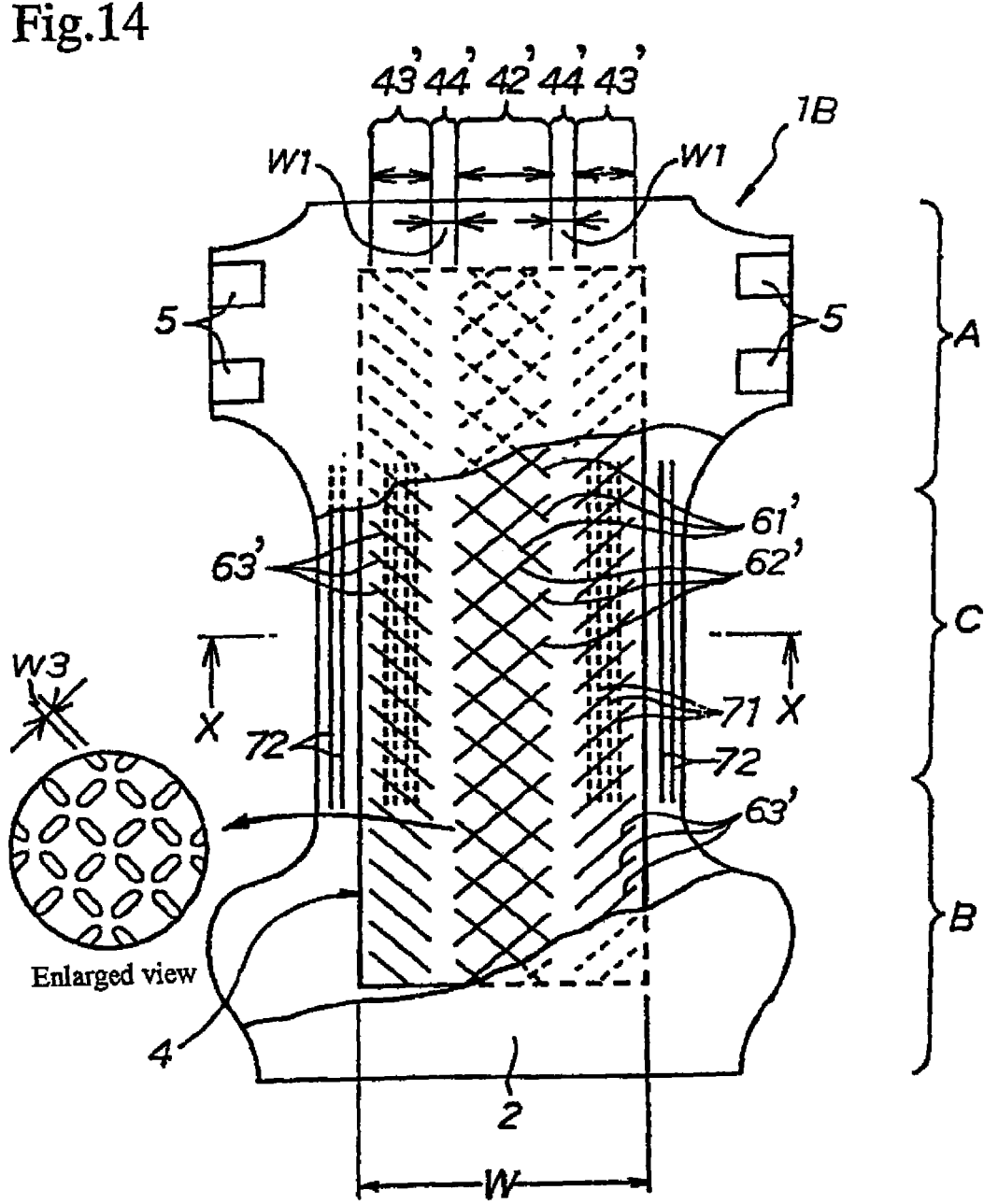
FIG. 14 is a plan of still another embodiment of the disposable diaper according to the invention with a part cut away.
Figure 15:
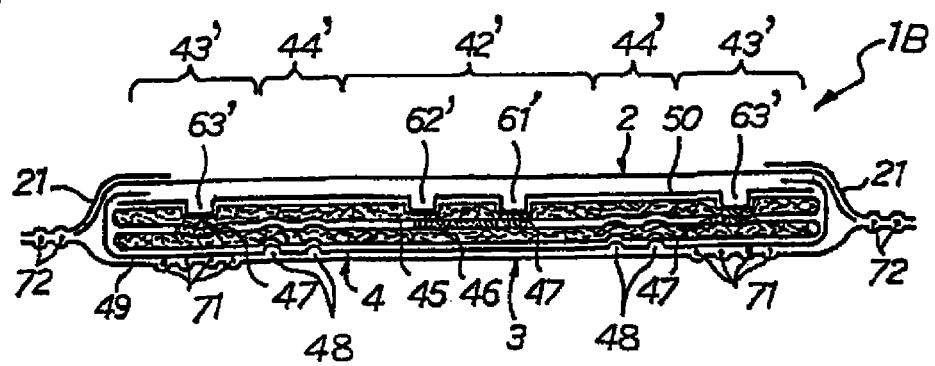
FIG. 15 is a schematic cross-section of the disposable diaper of FIG. 14, taken along line X-X.

The absorbent member 4 of the disposable diaper 1B shown in FIGS. 14 and 15 has a middle embossed portion 42' and side embossed portions 43' which are disposed on both sides of the middle embossed portion 42' with a space therebetween, each of these embossed portions extending in the longitudinal direction of the diaper 1B.

The middle embossed portion 42' and the side embossed portions 43' have embossed patterns on their topsheet 2 side. The embossed patterns of the middle is embossed portion 42' and the side embossed portions 43' are made up of a combination of slant linear depressions 61' and 62' and slant linear depressions 63', respectively, each slant linear depression crossing the longitudinal direction of the diaper 1B.

In more detail, the embossed pattern of the middle embossed portion 42' is made up of a plurality of parallel linear depressions 61' slanting downward to the right and a plurality of parallel linear depressions 62' slanting downward to the left. On a closer view, as is enlargedly illustrated on the left-hand side in FIG. 14, each of the linear depressions 61' and 62', while depicted as solid lines in FIG. 14, is made up of a chain of evenly spaced depressions, and the chains making the linear depressions 61' and the chains making the linear depressions 62' are crossing each other at their spacing. In other words, any two depressions do not cross each other. Such an embossing pattern gives moderate stiffness to the middle embossed portion 42'. On the other hand, each side embossed portion 43' has an embossed pattern of a plurality of parallel linear depressions 63' slanting downward to the right or to the left.

In order to impart moderate stiffness to the middle embossed portion 42' and the side embossed portions 43' so that the absorbent member 4 may surely bend in the area 44' between the middle embossed portion 42' and each side embossed portion 43' (hereinafter also referred to as an intermediate portion 44') in conformity to a wearer's body, it is preferred that the angle formed between the longitudinal direction of each linear depressions 61', 62' or 63' and the width direction of the diaper 1B is preferably 0 to 45°, still preferably 0 to 30°, and the width W3 (see the enlarged view in FIG. 14) of each depression is preferably 0.5 to 15 mm, still preferably 1 to 5 mm. From the same standpoint, the pitch of the linear depressions 63' in each side embossed portion 43' arranged along the longitudinal direction of the diaper 1B is preferably 3 to 35 mm, still preferably 5 to 20 mm, and the pitch of the linear depressions 61' or 62' in the middle embossed portion 42' along the longitudinal direction of the diaper 1B is preferably 20 to 70 mm, still preferably 30 to 50 mm.

From the same point of view, it is preferred that the ratio of the depth d1 of the depressions making the linear depressions 61', 62', and 63' to the thickness t of the surrounding non-embossed part of the absorbent member 4 (d1/t) be 0.1 to 0.7, particularly 0.3 to 0.5.

The intermediate portion 44' is not embossed on the topsheet 2 side thereof. In order for the absorbent member 4 to securely bend in the intermediate portion 44' and in order to minimize irritation to the groins and their vicinities, the width W1 (see FIG. 14) of the intermediate portion 44' in the crotch portion C is preferably 5 to 100 mm, still preferably 10 to 50 mm, and the ratio of the width W1 to the total width W of the absorbent member 4 in the crotch portion C, W1/W, is preferably 0.01 to 0.25, still preferably 0.03 to 0.15.

Figure 16:
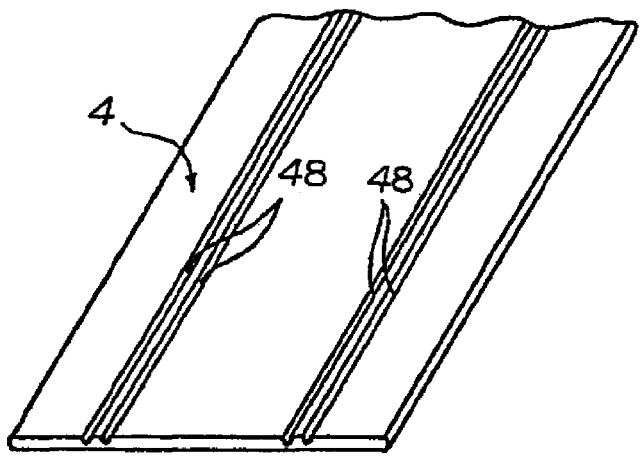
FIG. 16 is a partial perspective of the absorbent member in the disposable diaper of FIG. 14, viewed from the backsheet side.

Each of the intermediate portions 44' is embossed on the backsheet 3 side thereof to have a narrow linear depression 48 extending in the longitudinal direction of the portion 44' as shown in FIGS. 15 and 16. The diaper according to this particular embodiment has two crosswise spaced, substantially parallel linear depressions 48 on each intermediate portion 44' extending over the whole length of the absorbent member 4.

The linear depressions 48 formed on the intermediate portions 44' make the absorbent member 4 bend surely to an expected direction. Where, in particular, two or more crosswise spaced linear depressions 48 are formed on each intermediate portion 44', the angle of bending along each linear depression is reduced to improve bending capabilities, and the absorbent member 4 is capable of bending stably to an expected direction even though the size of a wearer or the manner of diapering somewhat varies.

To make sure that the absorbent member 4 bends to an expected direction, it is preferred that: the width of the linear depression 48 be 0.5 to 10 mm, particularly 0.8 to 3 mm; the pitch of the linear depressions 48, if there are two or more, be 3 to 20 mm, particularly 5 to 10 mm; and the linear depression 48 on each intermediate portion 44' be apart from the boundaries with the middle embossed portion 42' and with the side embossed portions 43', From the same point of view, the ratio of the depth d2 of the linear depression 48 to the thickness t of the surrounding non-embossed part of the absorbent member 4 (d2/t) is preferably 0.1 to 0.7, particularly 0.3 to 0.5.

Figure 17:
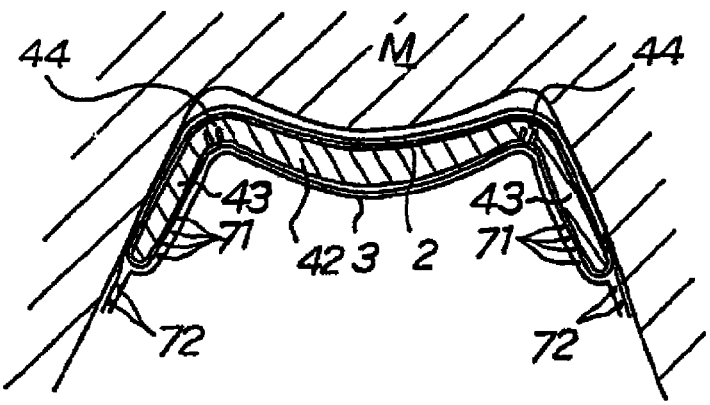
FIG. 17 is a schematic cross-section of the crotch portion of the disposable diaper of FIG. 14 while worn.

The diaper 1B is used just in the same way of diapering as with ordinary is disposable diapers. Put on a wearer, the absorbent member 4 in the crotch portion bends downward (toward the backsheet 3 side) to bring the side embossed portions 43' into contact with the inner side of wearer M's thighs as illustrated in FIG. 17.

According to the embodiment shown in FIGS. 14 to 17, the absorbent member 4 has the middle embossed portion 42' and the side embossed portions 43' and is designed to bend in the non-embossed intermediate portion 44' of prescribed width between these embossed portions. Unlike an absorbent member having no embossed pattern but the linear depression 48 on the backsheet 3 side as a bending axis, for instance, the absorbent member 4 of this embodiment securely bends in the intermediate portion 44' even where the size of a wearer or the manner of diapering somewhat changes.

Since the side embossed portions 43' exhibit moderate stiffness, it does not get turned up inside out while worn.

Thus, the inner side of the side embossed portions 43' is securely brought into contact with the inner side of wearer's thighs to provide a snug fit and excellent leakproof performance.

The diaper 1B has a plurality of parallel elastic members 71 provided in the part having each side embossed portion 43' along the longitudinal direction of that part. The elastic members 71 bring the side embossed portions 43' into intimate contact with the inner side of the thighs of a wearer to provide a snug fit and securely prevent leakage from the crotch portion C. The diaper 1B also has a second elastic member 72 extending in the longitudinal direction of the diaper within the crotch portion C at a position out of each lateral edge of the absorbent member 4 so that the parts having the elastic member 72 may come into close contact with wearer's thighs.

The absorbent member 4 of the diaper 1B shown in FIGS. 14 to 16 is composed of an upper fiber layer 45 and a lower fiber layer 46, and an absorbent polymer 47 disposed therebetween, the upper and lower fiber layers 45 and 46 being wrapped in between two liquid permeable sheets 49 and 50. The absorbent polymer 47 is disposed in each of the middle embossed portion 42' and the side embossed portions 43' in the crotch portion C to form a rectangular polymer layer extending in the longitudinal direction of the diaper 1B.

The angle or configuration of the linear depressions in the embossed portions of the diaper 1B is subject to variation. For example, while the linear depressions 63' of the side embossed portions 43' shown in FIG. 14 are slanted downward to the crosswise middle of the absorbent member 4, they may be slanted upward to the crosswise middle of the absorbent member 4. The linear depressions 61' 62', 63', and 48 formed by embossing may be either straight or not (e.g., wavy or zig-zaged) and may be either continuous or discontinuous.

The absorbent member 4 does not always need to be embossed over the whole length thereof as long as at least the crotch portion C is embossed to form the middle embossed portion 42' and the side embossed portions 43'. The bending capability of the intermediate portion 44' formed between the middle embossed portion 42' and the side embossed portions 43' may be limited to only a part of the length of the absorbent member 4. It is preferable that the bending capability be formed at least the crotch portion C. The elastic members 71 are disposed at any position in the thickness direction of the areas having the side embossed portions 43', for example, between the topsheet 2 and the absorbent member 4 or in the back of the backsheet 3.

Figure 18:
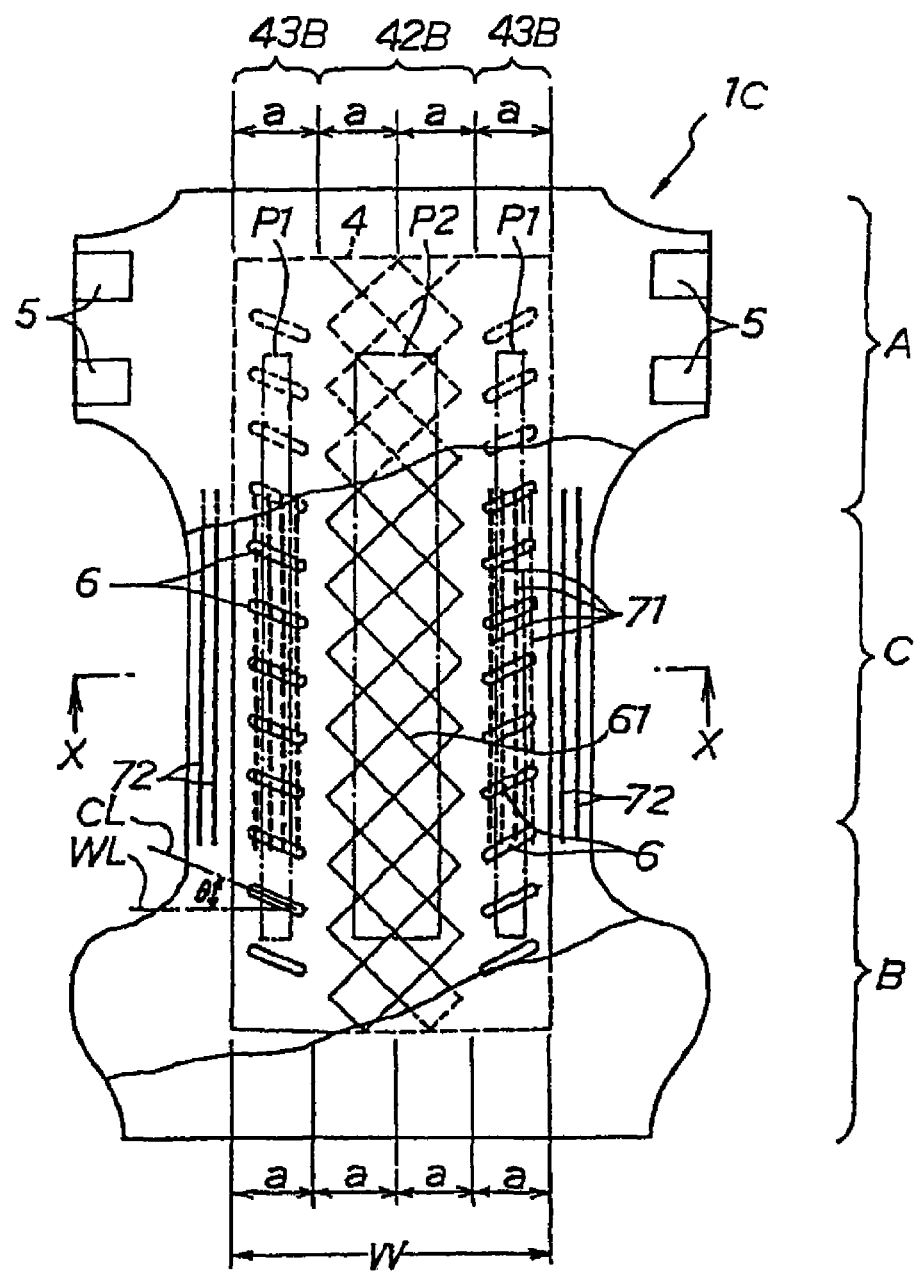
FIG. 18 is a plan of yet another embodiment of the disposable diaper according to the invention, with a part cut away.

In the disposable diaper 1C shown in FIG. 18, the area ratio of the joints between the absorbent member 4 and the backsheet 3 is varied in places. That is, the joint area ratio in two portions 43B which each occupy a prescribed width in crosswise side areas of the absorbent member 4 and extend in the longitudinal direction of the diaper 1C is smaller in the back portion A and/or the stomach portion B than in the crotch portion C, and an elastic member 71 is disposed in its stretched state in the crotch portion of each portion 43B along the longitudinal direction of the diaper 1C. In what follows, the term "joint area ratio" refers to the joint area ratio in the portions 43B.

Since the joint area ratio is smaller in the back portion A and/or the stomach portion B than in the crotch portion C, wrinkles generated on the backsheet 3 are inhibited from being reflected on the surface in contact with the wearer's skin or members disposed thereabouts, particularly the absorbent member 4, thereby reducing bunching of the absorbent member 4, etc. in the back portion A and/or the stomach portion B. As a result, development of skin troubles such as a bedsore can be reduced. Seeing that the crotch portion C directly faces the urination part of a wearer and is more liable to deformation by the movement of legs while worn, the higher joint area ratio of the portions 43B in the crotch portion C assures firm fixing of the absorbent member 4 in these portions to have the diaper exhibit stable absorbing performance.

For ensuring these effects, the joint area ratio in the back portion A and/or the stomach portion B is preferably 1 to 50%, still preferably 5 to 30%, and that in the crotch portion is preferably 15 to 85%, still preferably 30 to 60%. From the same point of view, the ratio of the joint area ratio in the back portion A and/or the stomach portion B to that in the crotch portion C, A/C and/or B/C, is preferably 0.01 to 0.8, still preferably 0.1 to 0.5.

Bunching of the absorbent member tends to occur when a wearer changes or is made to change from a supine position to a lateral position, and tends to occur particularly in the back portion Therefore, it is preferred for at least the back portion A to have a smaller joint area ratio than in the crotch portion C.

Figure 20:
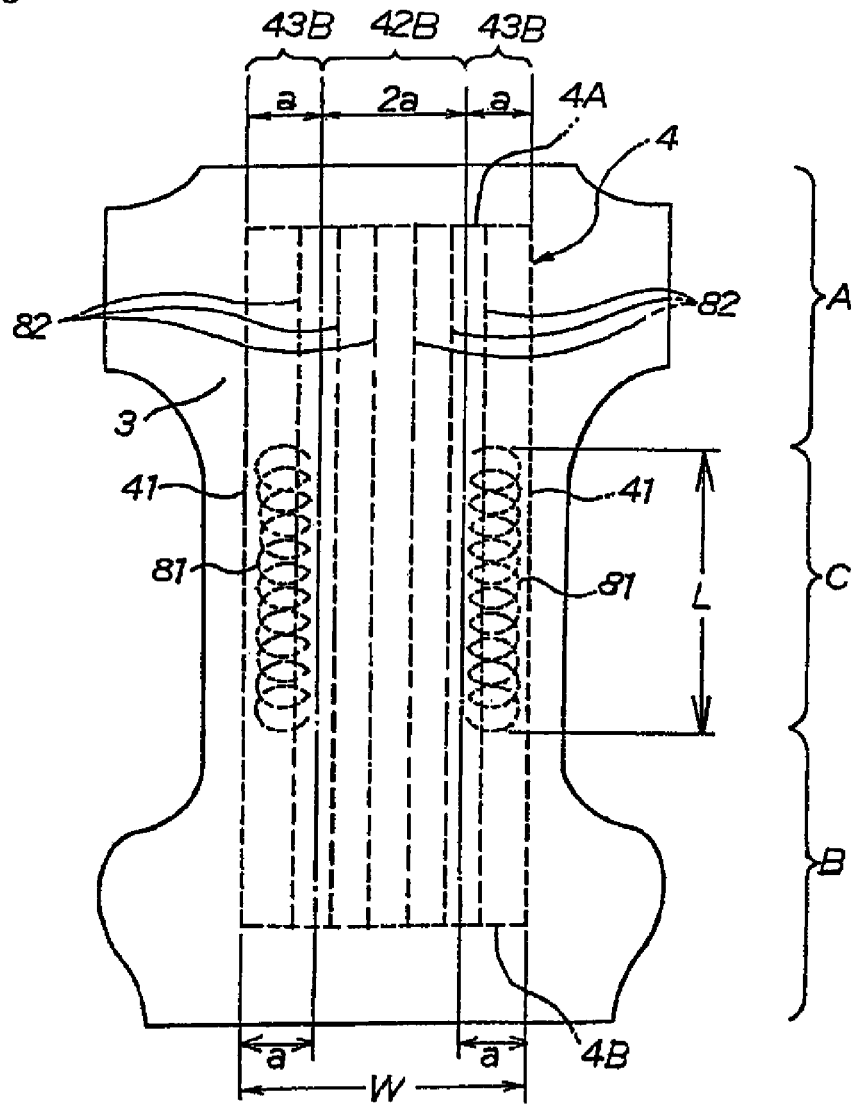
FIG. 20 is a back view showing the backsheet side of the disposable diaper shown in FIG. 19.
Figure 21:
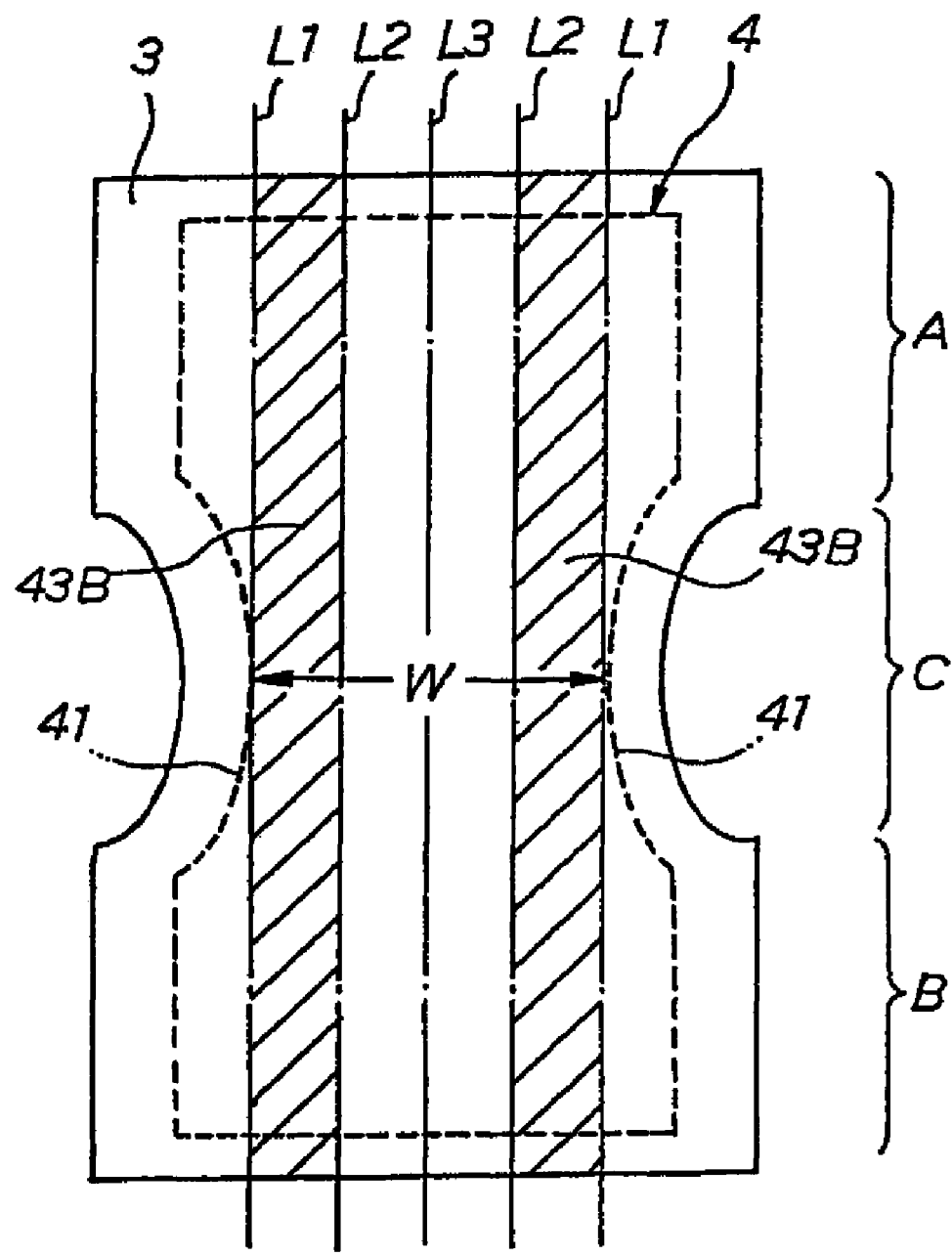
FIG. 21 schematically illustrates the essential part of an embodiment of the invention.

The portions 43B having a prescribed width as referred to here are oblong portions each extending in the longitudinal direction of the absorbent member 4 and occupying a left-hand or right-hand side quarter of the width of the area having the absorbent member 4 (the same as the width W of the absorbent member 4) as shown in FIGS. 18 and 20. In FIGS. 18 and 20, "a" indicates a quarter of the width W. The back portion A, the stomach portion B, and the crotch portion C as referred to with respect to this embodiment each occupy ⅓ of the total length of the disposable diaper 1C. The crotch portion C is the longitudinal middle between the back portion A and the stomach portion B.

Where the absorbent member 4 has a varied width along its length, for example, where both side edges 41 of the absorbent member 4 is curved inward in the crotch portion C as shown in FIG. 21, the shortest distance between both side edges of the absorbent member 4 in the crotch portion C is taken as the width W. In this case, five parallel lines (two lines L1, two lines L2, and one line L3) are drawn to vertically divide the width W into equal quarters as illustrated in FIG. 21, and the portions between the outermost lines L1 and the respective adjacent lines L2 are taken as the portions 43B. Where the absorbent member 4 is crosswise divided into separate sections as in the embodiment shown in FIG. 22, the shortest distance between the outer lateral edges 41 of the outermost sections is taken as the width W of the absorbent member 4.

Figure 22:
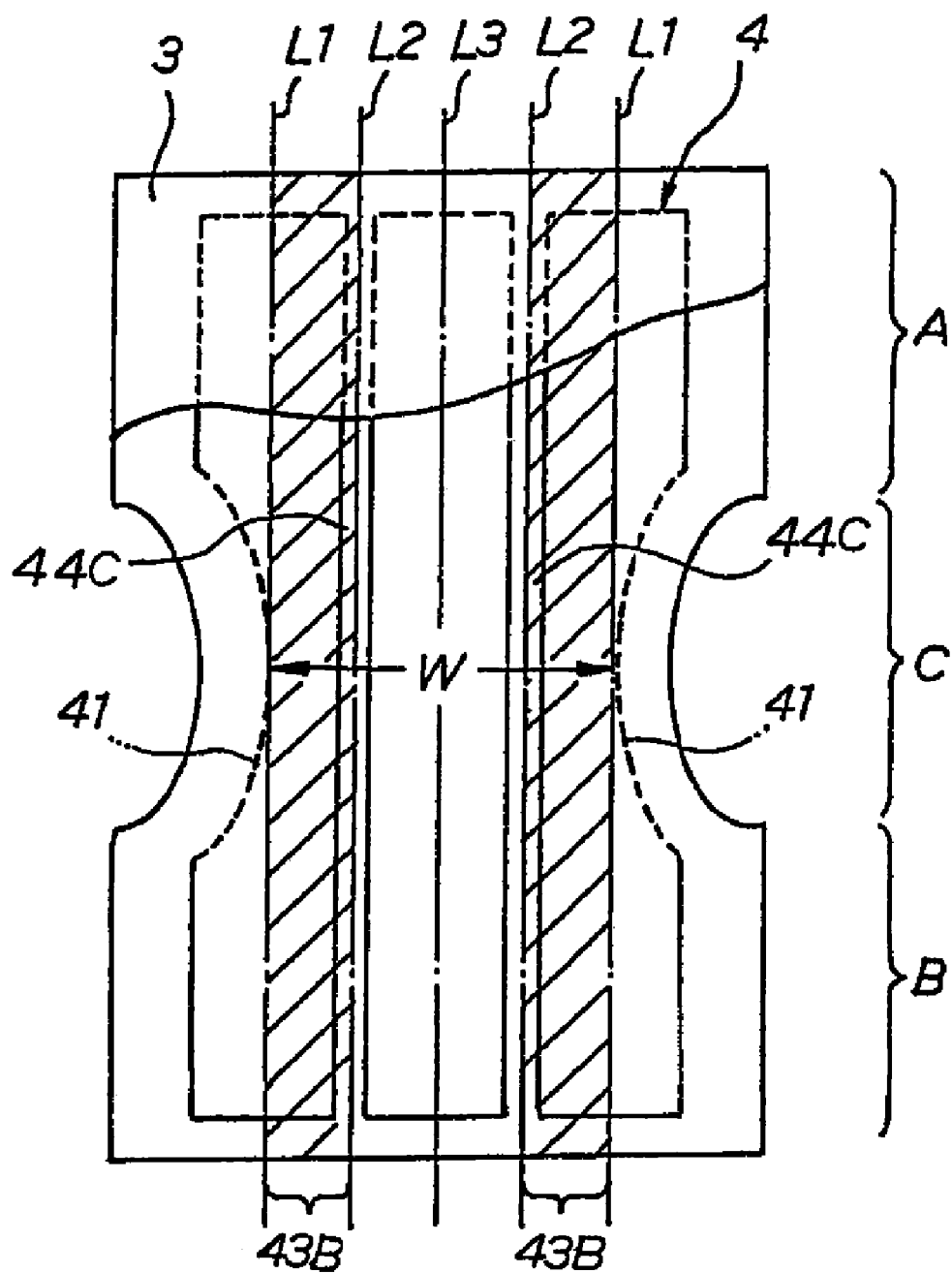
FIG. 22 schematically illustrates the essential part of another embodiment of the invention.

While not shown, a plurality of elastic members are provided in each of the portions 43B shown in FIGS. 21 and 22 similarly to the diaper 1 shown in FIGS. 1 through 3. In the diaper of FIG. 22, in which the absorbent member is divided in separate sections, the crosswise innermost one of the plurality of elastic members is disposed in each of non-absorbent portions 44C where no absorbent member exists, between two adjacent separate absorbent sections.

The joint area ratio in each of the back portion A, the stomach portion B, and the crotch portion C is measured as follows.

Joint Area Ratio in Back Portion A:

The total area of the parts of the portion 43B in the back portion A where the absorbent member 4 and the backsheet 3 exist is taken as an area R. The part of the area R where the absorbent member 4 and the backsheet 3 are joined together with a joining means, such as an adhesive (e.g., a hot-melt adhesive), heat seal or ultrasonic seal, is taken as a joint area S. The joint area ratio is obtained from equation:

Joint area ratio(%)=(joint area $S$/area $R$)×100

Joint Area Ratio in Crotch Portion C or Stomach Portion B:

The total area R of the parts of the portion 43B in the crotch portion C or the stomach portion B where the absorbent member 4 and the backsheet 3 exist and the joint area S in the portion C or B are measured, and the joint area ratio in each portion is obtained in the same manner as for the joint area ratio in the back portion A.

Figure 23A:
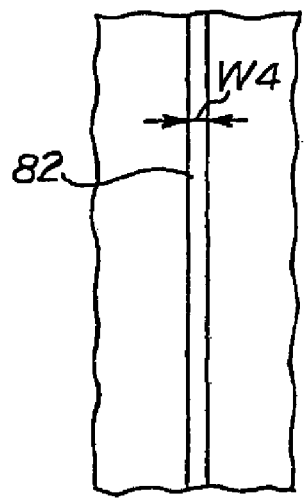
FIGS. 23(a) and 23(b) provide illustrations for measurement of a joint surface area.
Figure 23B:
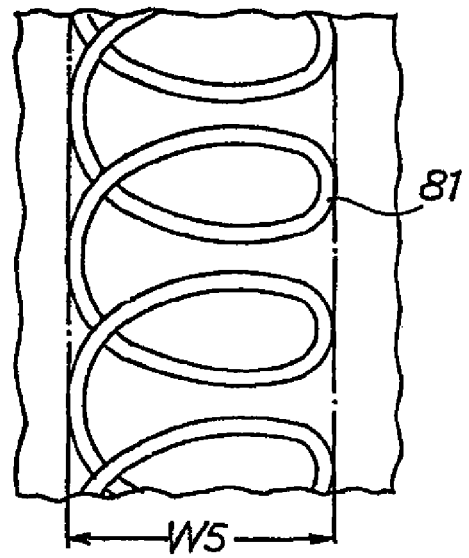

Measurement of Joint Area:

Where the absorbent member 4 and the backsheet 3 are joined by linear joining means 82 as shown in FIG. 23(a), the joint area is obtained by multiplying the average width W4 of the lines 82 by the total length of the lines existing in a portion. Where the absorbent member 4 and the backsheet 3 are joined by helical joining means 81 as shown in FIG. 23(b), the joint area is obtained by multiplying the average width W5 of the helical pattern measured in the width direction of the diaper by the total length of the pattern existing in a portion. In FIG. 20, the length of the helical pattern is indicated by symbol L. Where the length L exceeds the length of the crotch portion C, the part of the length L that is within the crotch portion is used for calculating the joint area S of the crotch portion. Where a linear or a helical pattern is made of a dotted line, the non-joint area between dots is included in the joint area.

Where, as shown in FIG. 22, the absorbent member 4 is crosswise divided into separate sections, and a side portion 43B contains a part of the non-absorbent portion 44C where no absorbent member exists, the area of this part of the non-absorbent portion 44C is assumed to be a part of the area R as far as the topsheet 2 and the backsheet 3 in this part of the portion 44C are joined together either directly or indirectly. In this case, the joint area in this part of the portion 44C is included in the joint area S, seeing that wrinkling or bunching of the backsheet 3 will be led to wrinkling or bunching of the topsheet 2.

In the disposable diaper 1C shown in FIG. 20, the absorbent member 4 and the backsheet 3 in the portions 43B are joined with an adhesive (as a joining means) applied in two different patterns (a first adhesive 81 and a second adhesive 82). The first adhesive 81 is applied in a wider pattern (with the width W5, see FIG. 23(b)) than the second adhesive 82 (with the width W4, see FIG. 23(a)). The application length of the first adhesive 81 is shorter than that of the second adhesive 82 so as not to reach the longitudinal ends 4A and 4B of the absorbent member 4 in the back portion A and the stomach portion B, respectively.

In more detail, the first adhesive 81 is applied in a helical pattern, and the second adhesive 82 is applied in a linear pattern. The first adhesive 81 is applied not only over the total length of the crotch portion C but to a slight length on the back portion A and the stomach portion B. On the other hand, the second adhesive 82 is applied over the whole length of the absorbent member 4.

The joining means is preferably an adhesive as used in this particular embodiment from the standpoint of joining performance, productivity, and the like. Other joining means, such as heat seal and ultrasonic seal, are also employable. The first and the second adhesives (joining means) may be the same or different in physical properties, the amount applied, and the like, except for the application (joint) pattern.

The adhesive (joining means) 81 applied in the crotch portion with a wider pattern width firmly fixes the absorbent member 4 in place. The adhesive (joining means) 82 applied in the back portion A and/or the stomach portion B with a narrower pattern width, particularly in a linear pattern (including wavy lines and broken lines) effectively attenuates the crosswise wrinkling force of the backsheet thereby reducing bunching of the absorbent member. These effects are pronouncedly produced particularly where the absorbent member 4 and the backsheet 3 are joined by a combination of the linearly applied adhesive 81 and the helically applied adhesive 81 in the crotch portion C and by the adhesive 82 applied in a single line or widely spaced lines in the back portion A and the stomach portion B as in the embodiment shown in FIG. 20.

As previously stated, the portions 43B in the crotch portion each have a plurality of elastic members 71 disposed in their stretched state in the longitudinal direction. As a result, the absorbent member 4 in the portions 43B in the crotch portion are gathered by contraction of the elastic members 71 and brought into close contact with the wearer's skin with a snug fit and are thereby prevented from bunching up. Accordingly, it is possible to reduce the amount of the adhesive to be applied for fixing the absorbent member 4 in the back portion A and the stomach portion B and to further reduce bunching of the absorbent member 4.

The topsheet 2 side (wearer's side) of the absorbent member 4 in the portions 43B of the diaper 1C is embossed to form linear depressions 6 as shown in FIG. 18. The linear depressions 6 each have a narrow, oblong elliptical shape whose longitudinal direction almost coincides with the width direction of the portions 43B. The linear depressions 6 exert resistance in the width direction of the absorbent member 4 thereby preventing the absorbent member from bunching up.

Such an effect of embossing is markedly manifested particularly when combining the helically applied adhesive 81.

For ensuring prevention of the absorbent member's bunching up and for improving the strength of the absorbent member, the angle θ (see FIG. 18) formed between the longitudinal direction of each linear depression 6 (indicated by centerline CL) and the width direction of the diaper 11C (indicated by line WL) is preferably 0 to 45°, still preferably 0 to 30°. The embossed pattern may be a pattern of straight lines (inclusive of dotted lines) as in the embodiment shown in FIG. 18, curved lines or a combination thereof. A straight line pattern is preferred for prevention of bunching and strength improvement.

The absorbent member 4 of the diaper 1C has a rectangular (in its plan view) laminate structure composed of an upper fiber layer 45 and a lower fiber layer 46. An absorbent polymer 47 is disposed between the upper fiber layer 45 and the lower fiber layer 46 in the areas having the linear depressions 6 to form a long and narrow polymer zone P1 which extends in the longitudinal direction of the diaper. It is preferred that the absorbent polymer 47 under the linear depressions 6 is crushed by embossing so that the embossed area may become harder to further ensure the resistance of the absorbent member 4 against bunching up.

Figure 19:
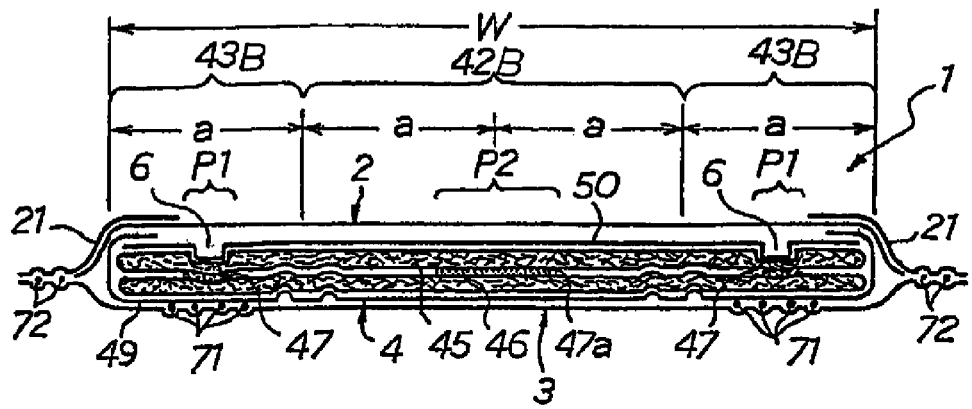
FIG. 19 is a schematic cross-section of the disposable diaper of FIG. 18, taken along line X-X.
Figure 24:
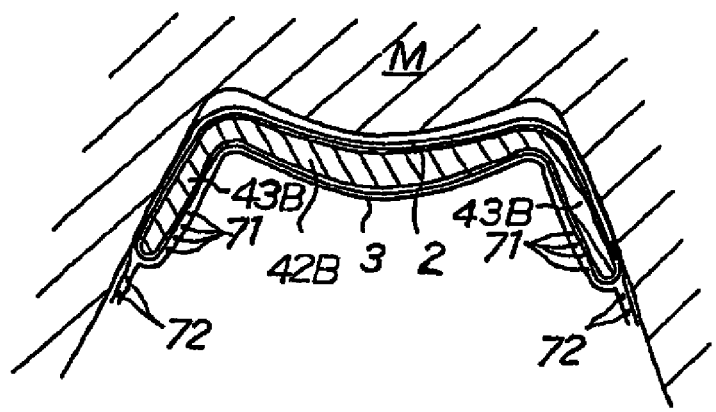
FIG. 24 is a schematic cross-section of the crotch portion of the disposable diaper of FIG. 18 while worn.

The disposable diaper 1C is designed so that the portions 43B in the crotch portion C may bend downward in conformity with the inner side of wearer M's thighs as illustrated in FIG. 24. The absorbent member 4 in the crosswise middle portion 42B (between the portions 43B) of the diaper 1C is embossed in a pattern (lattice pattern) different from the embossing pattern of the portions 43B (the lattice pattern is not shown in FIG. 19). An absorbent polymer 47a is disposed in the absorbent member 4 of the middle portion 42B to form a vertically oblong rectangular polymer zone P2. The absorbent member 4 has a laminate structure composed of the upper fiber layer 45 and the lower fiber layer 46, and the absorbent polymers 47 and 47a disposed therebetween. The laminate structure is wrapped in between two liquid permeable sheets 49 and 50. The diaper 1C also has a second elastic member 72 extending in the longitudinal direction of the diaper within the crotch portion C at a position out of each lateral edge 41 of the absorbent member 4 so that the parts having the elastic member 72 may come into close contact with wearer's thighs.

It is allowable for the diaper 1C to have no absorbent member 4 in its stomach portion B. In this case, the joint area ratio of the stomach portion is 0%. The elastic members 71 are disposed at any position in the thickness direction of the portions 43B, for example, between the topsheet 2 and the absorbent member 4 or in the back of the backsheet 3. While the disposable diaper according to the present invention is capable of conforming to a wearer's body when worn, the cross-sectional view of the bent absorbent member 4 is not limited to the M shape or inverted U shape as depicted in FIG. 24. For example, the absorbent member can bend into a U shape.

The aforementioned disposable diapers 1, 1', 1A, 1B, and 1C representing the preferred embodiments of the present invention will be described with respect to the materials making up their constituent members. The topsheet 2, the backsheet 3, the fastening tapes 5, the landing zone 51, and the adhesives 81 and 82 can be of any materials conventionally employed in disposable diapers. The backsheet 3 includes a laminate sheet composed of a liquid impermeable sheet and other sheeting.

The absorbent member 4 can be of any materials conventionally used in disposable diapers or like absorbent articles, including aggregates of fibers, such as pulp fiber, rayon, cellulose fiber, polyethylene fiber, and polypropylene fiber, aggregates of these fibers having an absorbent polymer distributed locally or uniformly, and fiber aggregates described above which are wrapped in paper, liquid permeable nonwoven fabric, etc. The absorbent polymer includes any kinds conventionally used in disposable diapers and like absorbent articles. A superabsorbent polymer capable of absorbing and retaining 20 times or more as much liquid as its own weight and capable of gelling is preferred. Such a superabsorbent polymer includes starch, crosslinked carboxymethylated cellulose, and homo- or copolymers of acrylic acid or an alkali metal salt thereof, such as polyacrylic acid or a salt thereof and a polyacrylate graft copolymer.

The elastic members 71 and 72 can be of natural rubber, synthetic rubber, and spundex (polyurethane fiber). The form of the elastic members includes a string, a tape, and a film. The elastic member 71 is preferably a rubber string or a rubber tape from the standpoint of contractibility, processability and cost. The hydrophobic sheets (backsheet 3 and the sheet 21) can be of any kind that has conventionally been used as a backsheet.

The present invention is by no means limited to the above-described embodiments, and various changes and modifications can be made therein without departing from the spirit and scope thereof.

For instance, the relationship between the middle absorbent portion 42 and the side absorbent portions 43 in terms of unit absorption capacity, etc., which is the characteristic of the crotch portion C of the disposable diaper according to the first aspect of the invention, is applicable to the whole length of the absorbent member.

Further, the lateral edge of each side absorbent portions 43 may be covered with two hydrophobic sheets (i.e., the backsheet 3 and the other sheet 21) as in the embodiment shown in FIG. 2 or with a single hydrophobic sheet.

Various known absorbent articles adapted to be placed on the inner side of a disposable diaper can be used in combination with the disposable diaper of the present invention.

Constitution of one embodiment which is not described and constituent elements characteristic of one embodiment are applicable to other embodiments. The constituent elements of the aforementioned embodiments are interchangeable among the embodiments.

The present invention provides a disposable diaper which can be produced at a lower cost and is excellent in leakproofness and fit.

The present invention provides a disposable diaper which is excellent in preventing leakage and holding an auxiliary absorbent article.

The present invention provides a disposable diaper which has a good fit to the inner side of wearer's thighs and excellent leakproof performance.

The present invention provides a disposable diaper, the absorbent member of which securely bends at an expected position in spite of slight variations of a wearer's 10 size or manner of diapering thereby secures a desired fit and/or leakproof performance. This effect is particularly marked where the disposable diaper is of the type in which at least a part of the inner surface of both lateral side portions of the absorbent member is brought into planar contact with the wearer's thighs while worn.

The present invention provides a disposable diaper in which the surface in contact with a wearer's body or a member disposed thereabouts, particularly the absorbent member greatly influential on the skin, hardly bunches up and therefore hardly causes skin troubles such as a bedsore.

The invention having being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A disposable diaper comprising a liquid permeable topsheet, a liquid impermeable backsheet, and a liquid retentive absorbent member and having a substantially oblong shape consisting of a back portion, a crotch portion, and a stomach portion, said absorbent member in the crotch portion having a middle absorbent portion which occupies 3/7 of the width of the absorbent member in the crotch portion and side absorbent portions which each occupy 1/7 of the width of the absorbent member in the crotch portion,
   wherein each of said side absorbent portions has a larger unit absorption capacity (g/cm$^2$) than said middle absorbent portion, wherein the difference of unit absorption capacity between the side absorbent portions and middle absorbent portion is 0.1 to 0.8 g/cm$^2$,
   one or two hydrophobic sheet(s) are disposed on the lateral outer edge of each of said side absorbent portions to cover from the upper to lower surfaces of said edge,
   an elastic member is disposed in the part having each of said side absorbent portions in the longitudinal direction of said side absorbent portions and further located at the back of said absorbent member between said liquid impermeable backsheet and a sheet forming the outer surface of the liquid retentive absorbent member,
   a plurality of compressed parts is formed in each side portion at intervals in the longitudinal direction of the side portions, and
   the elastic member is disposed across the plurality of compressed parts.

2. The disposable diaper according to claim 1, wherein said side absorbent portions each contain an absorbent polymer, and the part of each of said side absorbent portions which is covered with said hydrophobic sheet on the upper and the lower surfaces thereof has a smaller average absorbent polymer content than the whole side absorbent portion.

3. The disposable diaper according to claim 1, wherein the thickness of said middle absorbent portion is 2/3 or smaller of the thickness of each of said side absorbent portions.

4. The disposable diaper according to claim 1, wherein a low stiff part is formed between said middle absorbent portion and each of said side absorbent portions in the longitudinal direction.

5. The disposable diaper according to claim 1, which is adapted to be used in combination with an auxiliary absorbent article placed on the inner side of the diaper, wherein an indicator visually distinguishable when viewed from the inner side of the diaper is disposed near each lateral edge of said absorbent member in the crotch portion.

6. The disposable diaper according to claim 1, wherein said middle absorbent portion is in the crosswise middle of said absorbent member in the crotch portion, and each of said side absorbent portions is positioned on the side of said middle absorbent portion via an intermediate portion occupying 1/7 of the width of said absorbent member.

7. The disposable diaper according to claim 1, wherein both side portions of said absorbent member in the crotch portion bend downward in conformity with the inner side of wearer's thighs while worn, and a plurality of compressed parts are formed on each of said side portions at intervals in the longitudinal direction.

8. The disposable diaper according to claim 7, wherein each of said compressed parts extend substantially in the width direction of the diaper.

9. The disposable diaper according to claim 7, wherein an elastic member is provided in the stretched state thereof in a part having each of said side portions across a plurality of said compressed parts.

10. The disposable diaper according to claim 7, wherein said compressed parts are formed by pressing the topsheet side of said absorbent member by embossing.

11. The disposable diaper according to claim 7, wherein each of said side portions has a laminate structure composed of a plurality of absorbent layers, an absorbent polymer is disposed between said absorbent layers in each of said side portions to form a polymer zone extending in the longitudinal direction of said side portion, at least one of said compressed parts is formed in each area where said polymer zone lies, and at least one compressed part is formed at a position out of each longitudinal end of each of said polymer zones.

12. The disposable diaper according to claim 1, wherein said absorbent member has a middle embossed portion, side embossed portions disposed on both sides of said middle embossed portion, and an intermediate portion disposed between said middle embossed portion and each of said side embossed portions, each of said middle and side embossed portions having the topsheet side thereof embossed and extending in the longitudinal direction of the diaper, and said absorbent member bends downward in said intermediate portion while worn.

13. The disposable diaper according to claim 12, wherein said intermediate portion has the backsheet side thereof embossed to have a narrow linear depression extending in the longitudinal direction thereof.

14. The disposable diaper according to claim 13, wherein said intermediate portion has two or more said linear depressions which are crosswise spaced.

15. The disposable diaper according to claim 12, wherein an elastic member is provided in the part having each of said side embossed portions in the longitudinal direction of said side embossed portions.

16. The disposable diaper according to claim 12, wherein said middle embossed portion and said side embossed portions each have on the topsheet side thereof at least linear depressions which are across the longitudinal direction of the diaper.

17. The disposable diaper according to claim 1, wherein the difference of unit absorption capacity between the side absorbent portions and middle absorbent portion is 0.1 to 0.4 g/cm$^2$.

18. The disposable diaper according to claim 1, wherein the unit absorption capacity of the side absorbent portions is 0.1 to 0.8 g/cm$^2$.

19. The disposable diaper according to claim 1, wherein the unit absorption capacity of the side absorbent portions is 0.1 to 0.4 g/cm$^2$.

20. The disposable diaper according to claim 1, wherein said middle and side absorbent portions comprise an absorbent polymer;
   wherein each of said side absorbent portions has a higher content of the absorbent polymer versus the middle absorbent portion; and
   wherein each of said side absorbent portions has an average content of 20 to 150 g/m$^2$ of said absorbent polymer.

21. The disposable diaper according to claim 20, wherein the middle portion has an average content of 0 to 100 g/m$^2$ of said absorbent polymer.

22. The disposable diaper according to claim 20, wherein said absorbent polymer is a superabsorbent polymer selected from the group comprising starch, crosslinked carboxymethylated cellulose, a homopolymer of acrylic acid or an alkali metal thereof, and a copolymer of acrylic acid or an alkali metal salt thereof.

23. A disposable diaper comprising a liquid permeable topsheet, a liquid impermeable backsheet, and a liquid retentive absorbent member and having a substantially oblong shape consisting of a back portion, a crotch portion, and a stomach portion, said absorbent member in the crotch portion having a middle absorbent portion which occupies $3/7$ of the width of the absorbent member in the crotch portion and side absorbent portions which each occupy $1/7$ of the width of the absorbent member in the crotch portion, wherein each of said side absorbent portions has a larger unit absorption capacity (g/cm$^2$) than said middle absorbent portion, one or two hydrophobic sheet(s) are disposed on the lateral outer edge of each of said side absorbent portions to cover from the upper to lower surfaces of said edge, an elastic member is disposed in the part having each of said side absorbent portions in the longitudinal direction of said side absorbent portions, and further located at the back of said absorbent member between said liquid impermeable backsheet and a sheet forming the outer surface of the liquid retentive absorbent member, a plurality of compressed parts is formed in each side portion at intervals in the longitudinal direction of the side portions, and the elastic member is disposed across the plurality of compressed parts.

24. The disposable diaper according to claim 23, wherein the difference of unit absorption capacity between the side absorbent portions and middle absorbent portion is 0.1 to 0.4 g/cm$^2$.

* * * * *